US009782316B2

(12) United States Patent
Schuerch, Jr. et al.

(10) Patent No.: US 9,782,316 B2
(45) Date of Patent: Oct. 10, 2017

(54) ADJUSTABLE-POSITION LIMB AND/OR INSTRUMENT SUPPORT ARM FOR MEDICAL TABLES

(71) Applicants: Peter E. Schuerch, Jr., Quincy, MA (US); Hermanus Stephanus Pretorius, Derry, NH (US)

(72) Inventors: Peter E. Schuerch, Jr., Quincy, MA (US); Hermanus Stephanus Pretorius, Derry, NH (US)

(73) Assignee: Peter E. Schuerch, Jr., Quincy, MA (US)

( * ) Notice: Subject to any disclaimer, the term of this patent is extended or adjusted under 35 U.S.C. 154(b) by 0 days.

(21) Appl. No.: 15/150,726

(22) Filed: May 10, 2016

(65) Prior Publication Data

US 2017/0095387 A1 Apr. 6, 2017

Related U.S. Application Data

(63) Continuation of application No. 14/167,775, filed on Jan. 29, 2014, now Pat. No. 9,333,142.
(Continued)

(51) Int. Cl.
*A61G 13/12* (2006.01)
*A61G 13/10* (2006.01)
(Continued)

(52) U.S. Cl.
CPC ....... *A61G 13/101* (2013.01); *A61G 13/1235* (2013.01); *A61G 13/1245* (2013.01);
(Continued)

(58) Field of Classification Search
CPC ............................ A61G 13/12; A61G 13/1205
(Continued)

(56) References Cited

U.S. PATENT DOCUMENTS

| 4,308,419 A | 12/1981 | Fredriksson |
| 4,426,071 A | 1/1984 | Klevstad |

(Continued)

FOREIGN PATENT DOCUMENTS

CN 201870867 6/2011

OTHER PUBLICATIONS

TRIMANO Support Arm, 2011 Arthrex GmbH.
Arthroscopy Limb Positioners, Limb Positioners for Hip, Knee, Distal Extremities and Shoulder, 2013, Arthrex Inc.

*Primary Examiner* — Fredrick Conley
(74) *Attorney, Agent, or Firm* — Pandiscio & Pandiscio

(57) ABSTRACT

An adjustable-position support arm comprising a plurality of tubular elements connected to one another in series of joints; a locking mechanism disposed at each joint so that a first portion of the locking mechanism is secured to a first tubular element of that joint and a second portion of the locking mechanism is secured to the second tubular element of that same joint wherein the locking mechanism is configured in a locked condition to prevent rotation of the first tubular element relative to the second tubular element selectively unlocked condition so that the first tubular element is rotatable relative to the second tubular element; and an actuator for actuating all of the locking mechanisms from their locked condition to their unlocked condition.

24 Claims, 36 Drawing Sheets

Related U.S. Application Data

(60) Provisional application No. 61/757,933, filed on Jan. 29, 2013.

(51) Int. Cl.

| | | |
|---|---|---|
| *F16M 13/02* | (2006.01) | |
| *F16M 11/06* | (2006.01) | |
| *F16M 11/20* | (2006.01) | |
| *F16C 11/10* | (2006.01) | |
| *A61B 90/57* | (2016.01) | |

(52) U.S. Cl.
 CPC ............. *F16C 11/10* (2013.01); *F16M 11/06* (2013.01); *F16M 11/2035* (2013.01); *F16M 13/02* (2013.01); *A61B 2090/571* (2016.02); *F16M 2200/024* (2013.01)

(58) Field of Classification Search
 USPC .................................................... 5/621–624
 See application file for complete search history.

(56) References Cited

U.S. PATENT DOCUMENTS

| | | | |
|---|---|---|---|
| 5,775,334 A | * | 7/1998 | Lamb ................... A61G 13/12 128/845 |
| 5,961,512 A | | 10/1999 | Purnell |
| 6,058,534 A | | 5/2000 | Navarro et al. |
| RE41,412 E | | 7/2010 | Van Steenburg |
| 2004/0143243 A1 | | 7/2004 | Wahrburg |
| 2008/0121765 A1 | | 5/2008 | Fetzer |
| 2008/0215065 A1 | | 9/2008 | Wang et al. |
| 2009/0236484 A1 | | 9/2009 | Koch et al. |
| 2010/0030377 A1 | | 2/2010 | Unsworth |
| 2012/0010629 A1 | | 1/2012 | Mire et al. |
| 2012/0174318 A1 | * | 7/2012 | Vestergaard ............ A47C 7/40 5/613 |
| 2012/0197182 A1 | | 8/2012 | Millman et al. |
| 2012/0209291 A1 | | 8/2012 | Anderson et al. |
| 2012/0253513 A1 | | 10/2012 | Unsworth |

* cited by examiner

ADJUSTABLE-POSITION LIMB AND/OR INSTRUMENT SUPPORT ARM FOR MEDICAL TABLES

REFERENCE TO PENDING PRIOR PATENT APPLICATIONS

This patent application is a continuation of pending prior U.S. Patent Application Ser. No. 14/167,775, filed 01/29/2014 by Peter E. Schuerch, Jr. for ADJUSTABLE-POSITION LIMB AND/OR INSTRUMENT SUPPORT ARM FOR MEDICAL TABLES, which patent application in turn claims benefit of prior U.S. Provisional Patent Application Ser. No. 61/757,933, filed Jan. 1, 2013 by Peter Schuerch, Jr. for ADJUSTABLE-POSITION LIMB AND INSTRUMENT SUPPORT SYSTEM FOR SURGICAL TABLES The above-identified patent applications are hereby incorporated herein by reference.

FIELD OF THE INVENTION

This invention relates to medical apparatus and procedures in general, and more particularly to adjustable-position limb and/or instrument support arms for medical tables.

BACKGROUND OF THE INVENTION

When a patient is undergoing a medical procedure, it may be necessary and/or desirable to provide a support arm, for attachment to a medical table, for positioning and supporting a patient's limb (e.g., during shoulder surgery) and/or for positioning and supporting medical instruments (e.g., endoscopes, laparoscopes, etc.), etc. In general, it is important that this support arm be capable of adjustable positioning so as to accommodate a wide range of different patient needs and be capable of reliably maintaining its position under substantial load (e.g., while holding a limb in traction).

Conventional adjustable-position limb and/or instrument support arms for medical tables tend to suffer from a limited range of motion, slippage during use, high cost, etc.

Thus there is a need for a new adjustable-position limb and/or instrument support arm for medical tables which provides a wide range of motion, reliably maintains its position during use, is relatively low in cost, etc.

SUMMARY OF THE INVENTION

The present invention provides a new adjustable-position limb and/or instrument support arm for medical tables which provides a wide range of motion, reliably maintains its position during use, is relatively low in cost, etc.

In one preferred form of the present invention, there is provided an adjustable-position support arm for a medical table, the adjustable-position support arm comprising:

a plurality of tubular elements connected to one another in series at a plurality of joints;

a locking mechanism disposed at each joint so that a first portion of the locking mechanism is secured to a first tubular element of that joint and a second portion of the locking mechanism is secured to the second tubular element of that same joint, wherein the locking mechanism is normally configured in a locked condition so as to prevent rotation of the first tubular element relative to the second tubular element, and further wherein the locking mechanism may be selectively reconfigured in an unlocked condition so that the first tubular element is rotatable relative to the second tubular element; and an actuator for simultaneously reconfiguring all of the locking mechanisms from their locked condition to their unlocked condition, whereby to permit the plurality of tubular elements to be rotated about the plurality of joints.

In another preferred form of the present invention, there is provided a method for adjustably supporting an object about a medical table, the method comprising:

providing an adjustable-position support arm, the adjustable-position support arm comprising:

a plurality of tubular elements connected to one another in series at a plurality of joints;

a locking mechanism disposed at each joint so that a first portion of the locking mechanism is secured to a first tubular element of that joint and a second portion of the locking mechanism is secured to the second tubular element of that same joint, wherein the locking mechanism is normally configured in a locked condition so as to prevent rotation of the first tubular element relative to the second tubular element, and further wherein the locking mechanism may be selectively reconfigured in an unlocked condition so that the first tubular element is rotatable relative to the second tubular element; and an actuator for simultaneously reconfiguring all of the locking mechanisms from their locked condition to their unlocked condition, whereby to permit the plurality of tubular elements to be rotated about the plurality of joints;

securing the adjustable-position support arm to a medical table;

activating the actuator to simultaneously reconfigure all of the locking mechanisms from their locked condition to their unlocked condition, and rotating at least some of the plurality of tubular elements about their associated joints.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a new adjustable-position limb and/or instrument support arm for medical tables which provides a wide range of motion, reliably maintains its position during use, is relatively low in cost, etc.

Cable-Based Adjustable-Position Support Arm

Figure 11:
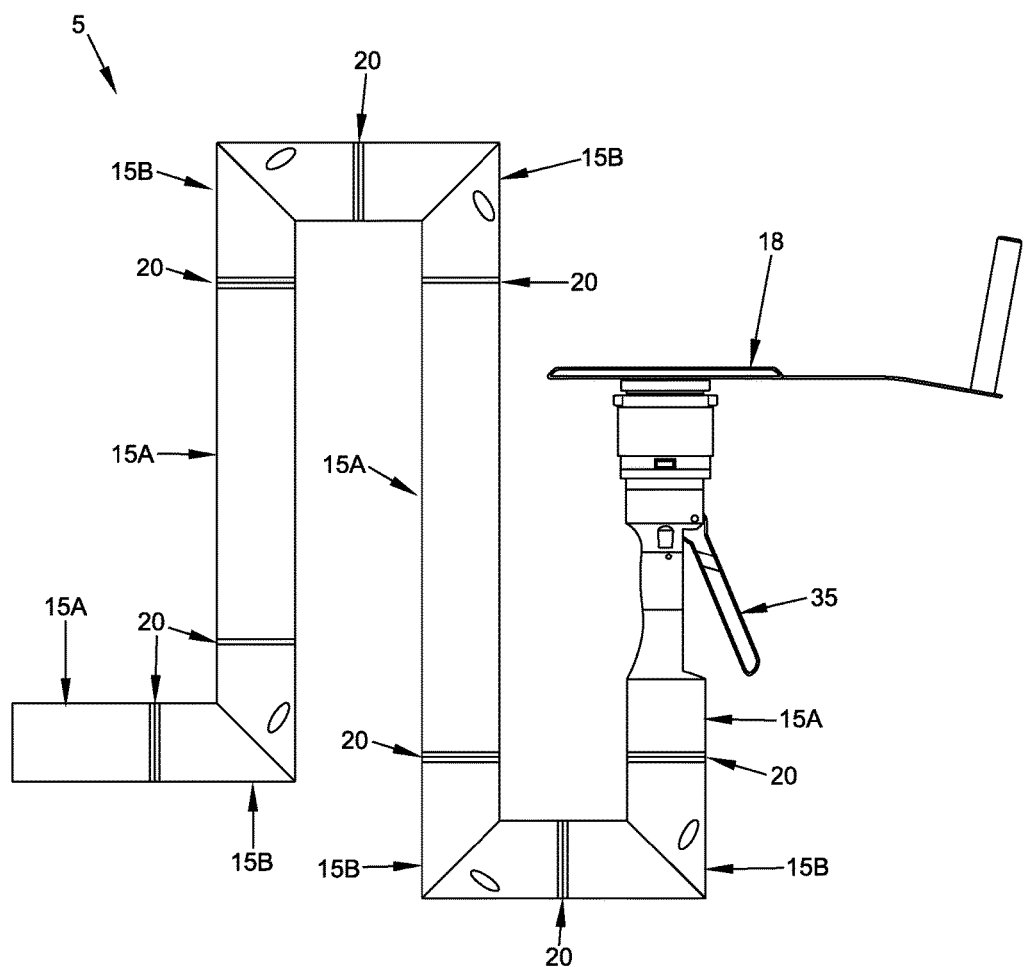
FIGS. 11-15 are schematic views showing another form of an adjustable-position support arm formed in accordance with the present invention.
Figure 12:
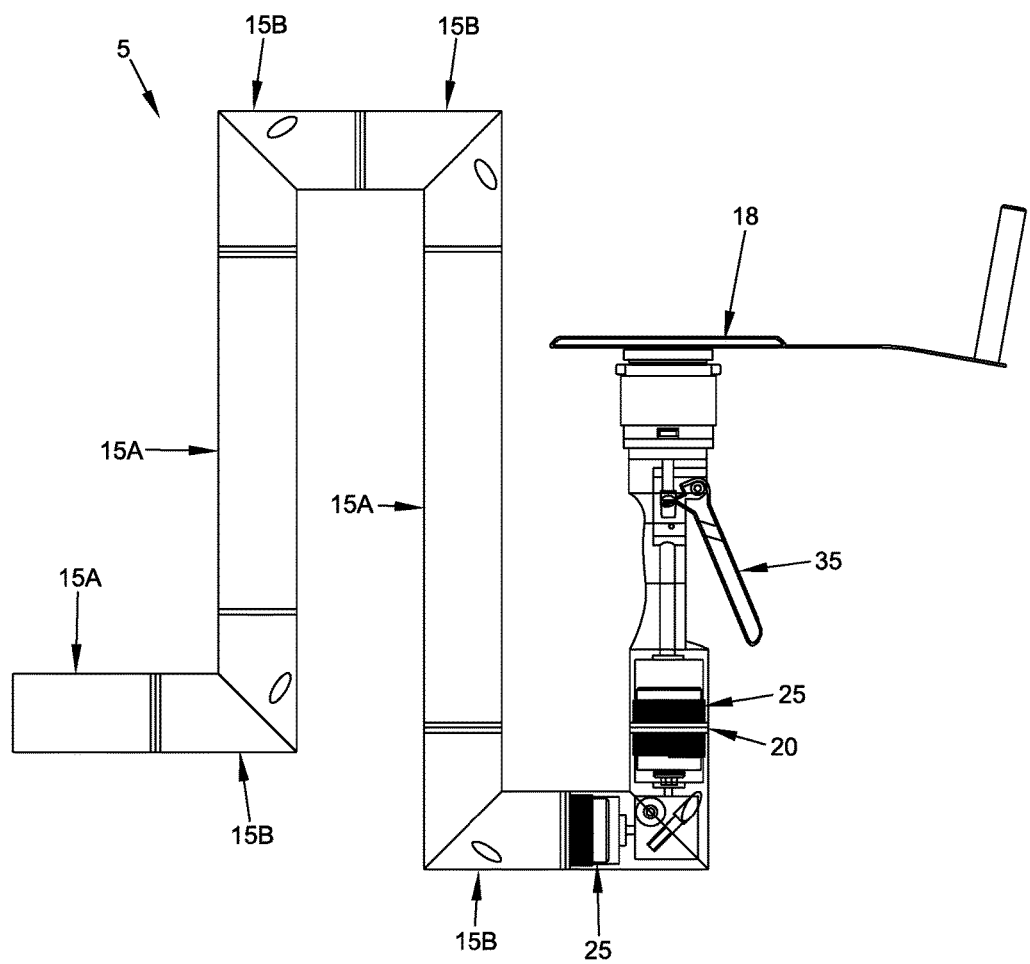
Figure 13:
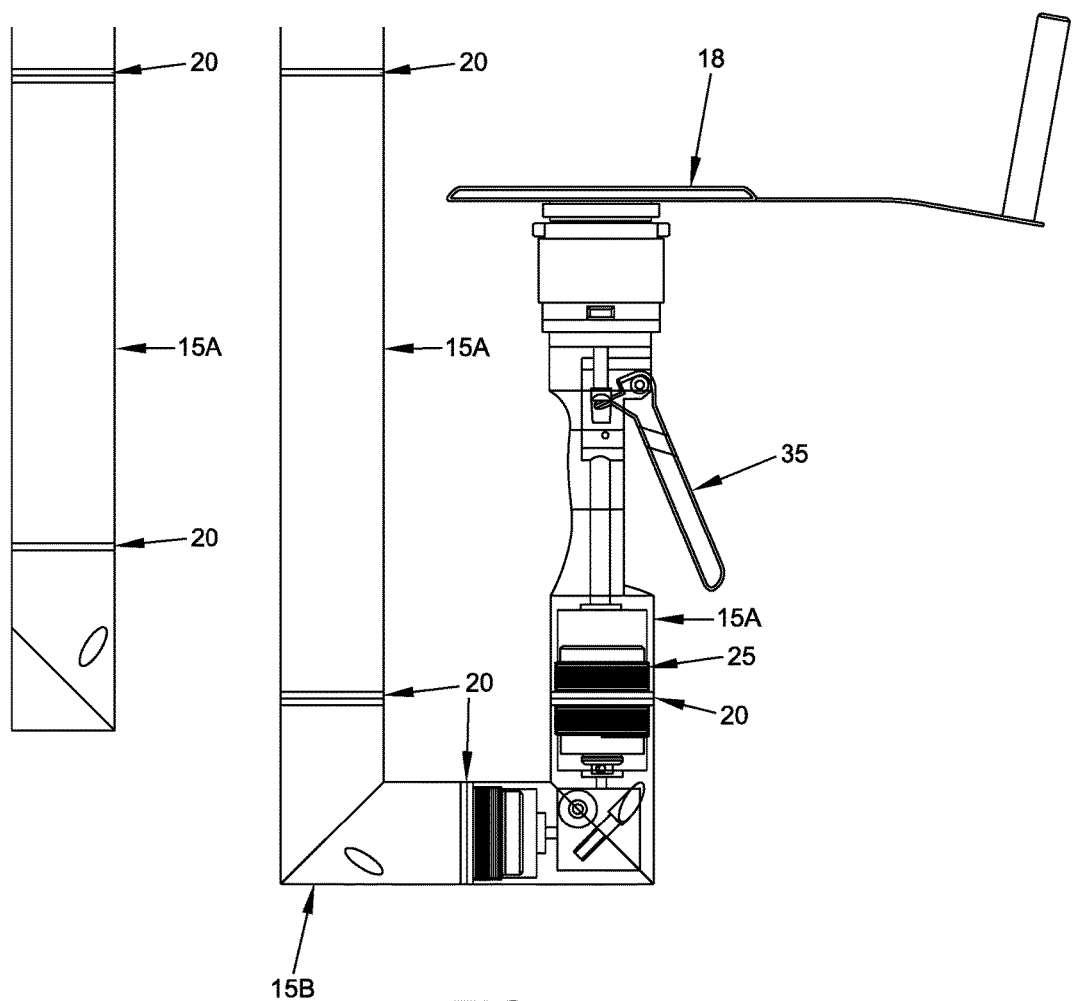
Figure 14:
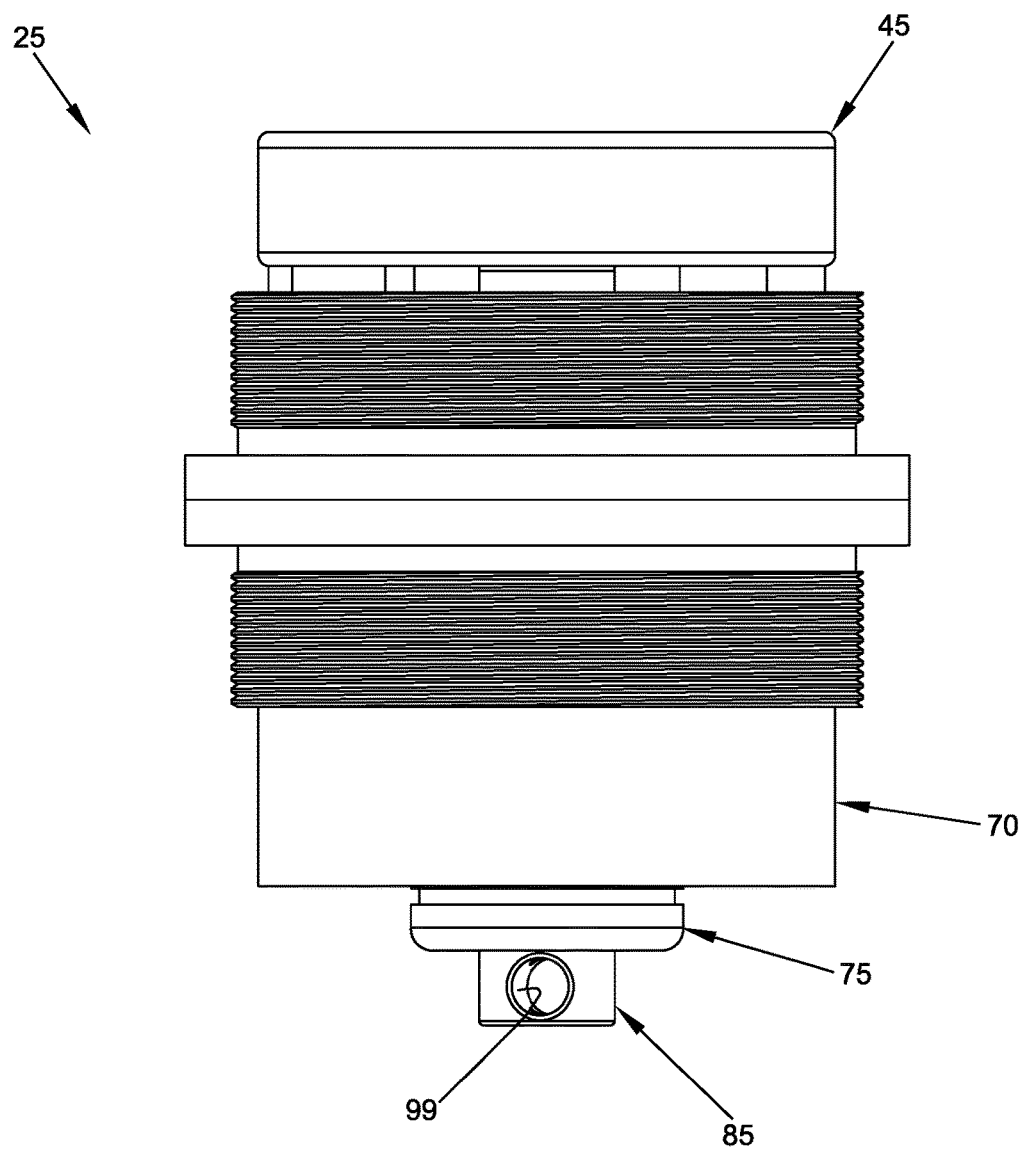
Figure 15:
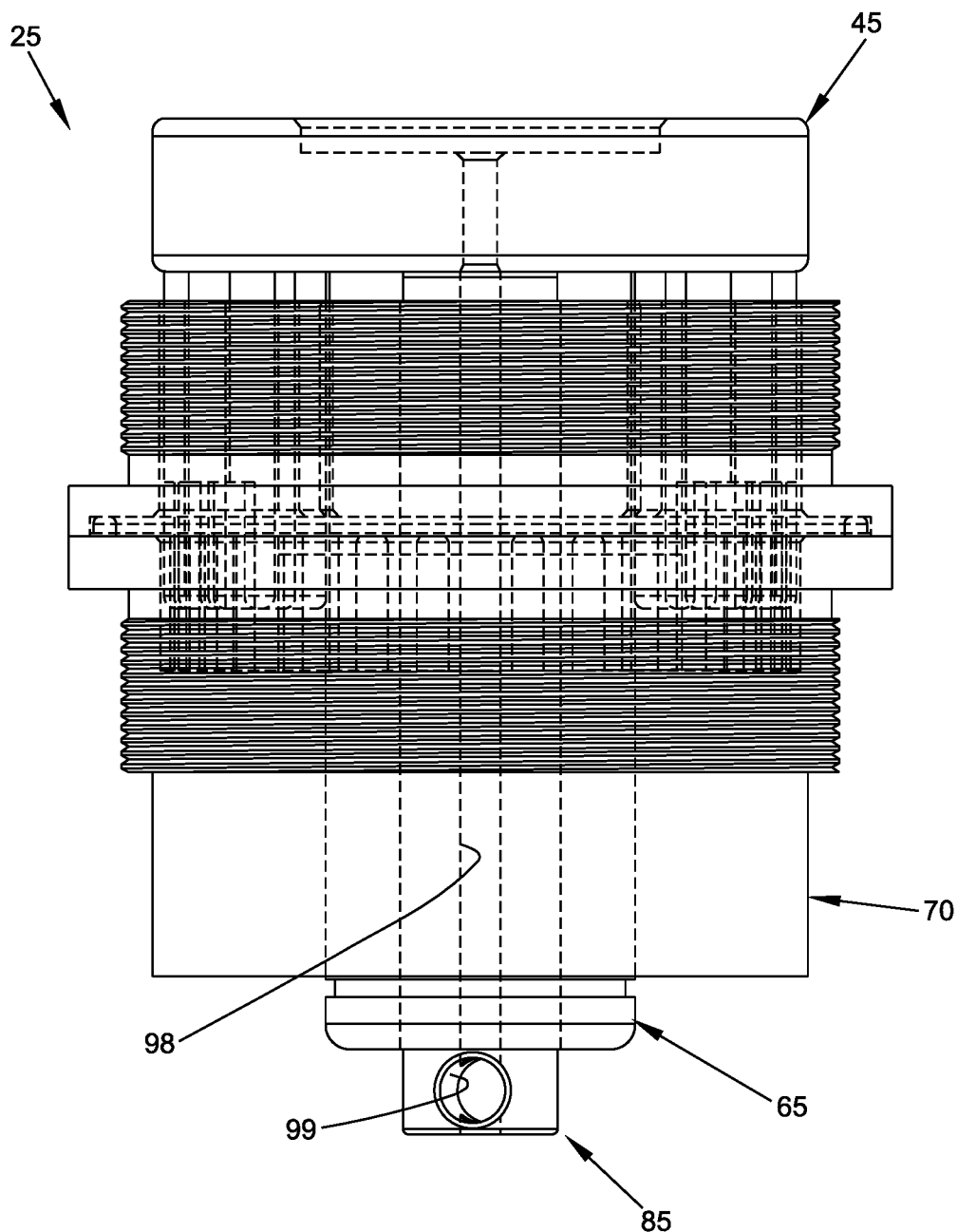
Figure 16:
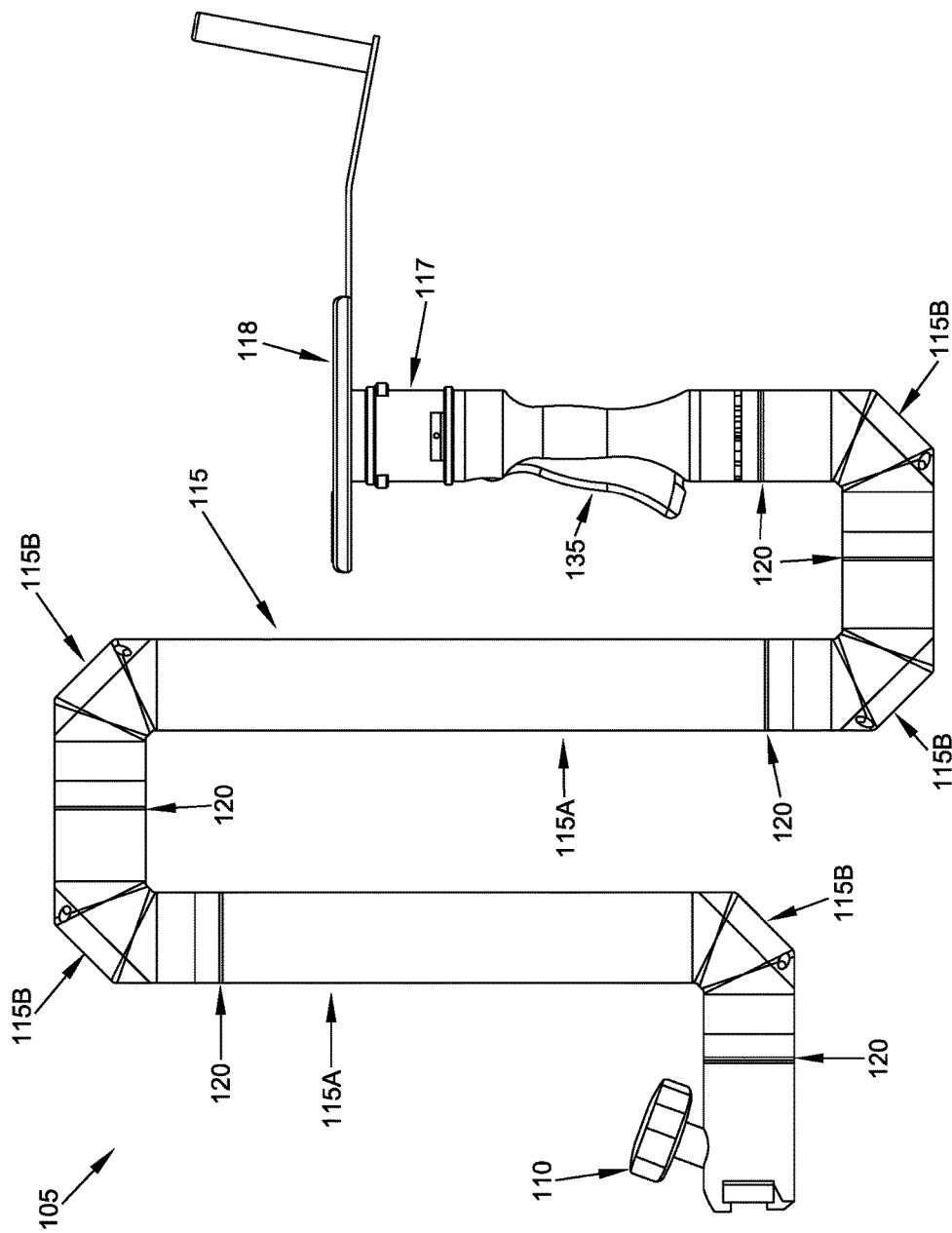
FIGS. 16-36 are schematic views showing another form of an adjustable-position support arm formed in accordance with the present invention.
Figure 17:
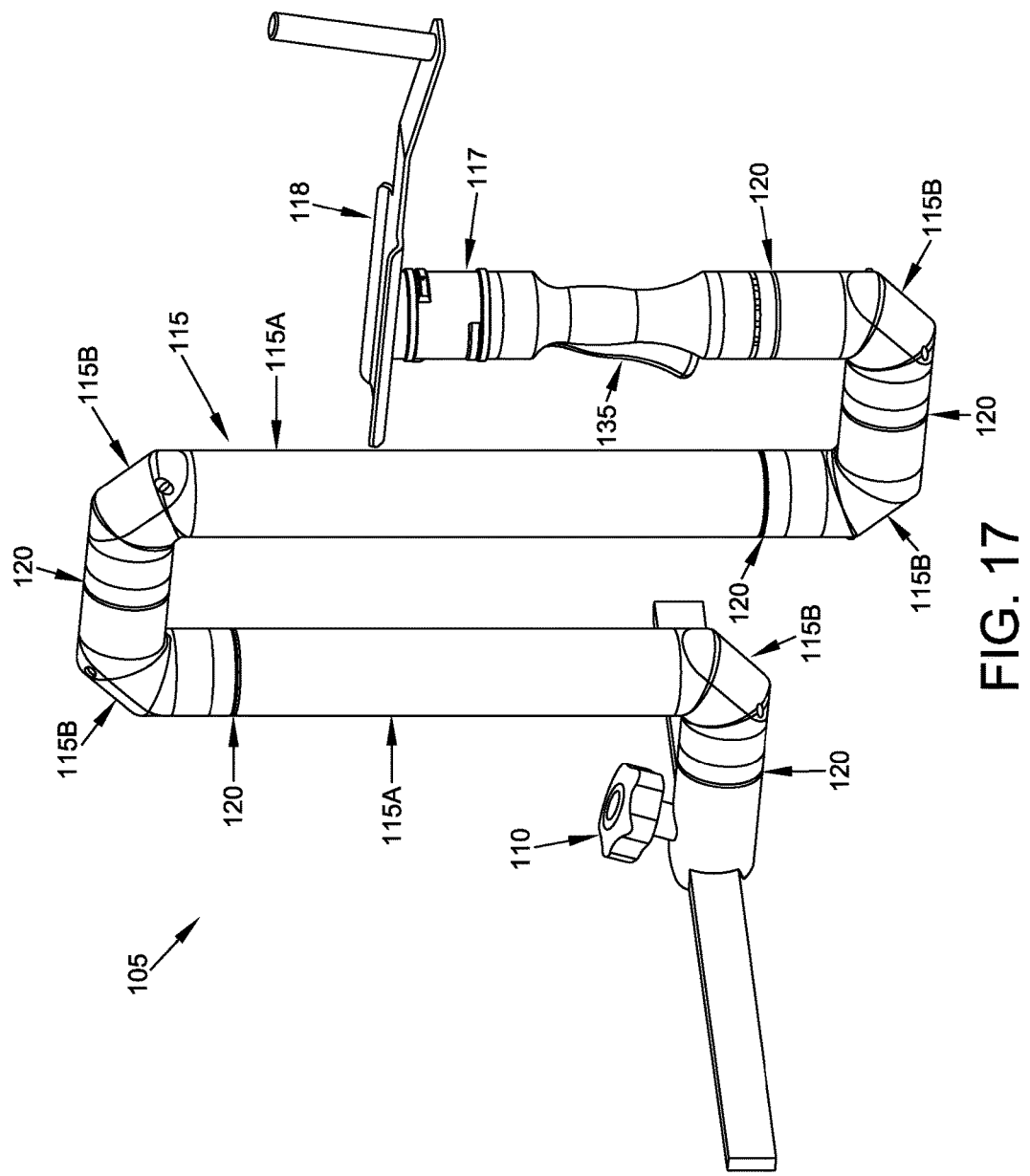
Figure 18:
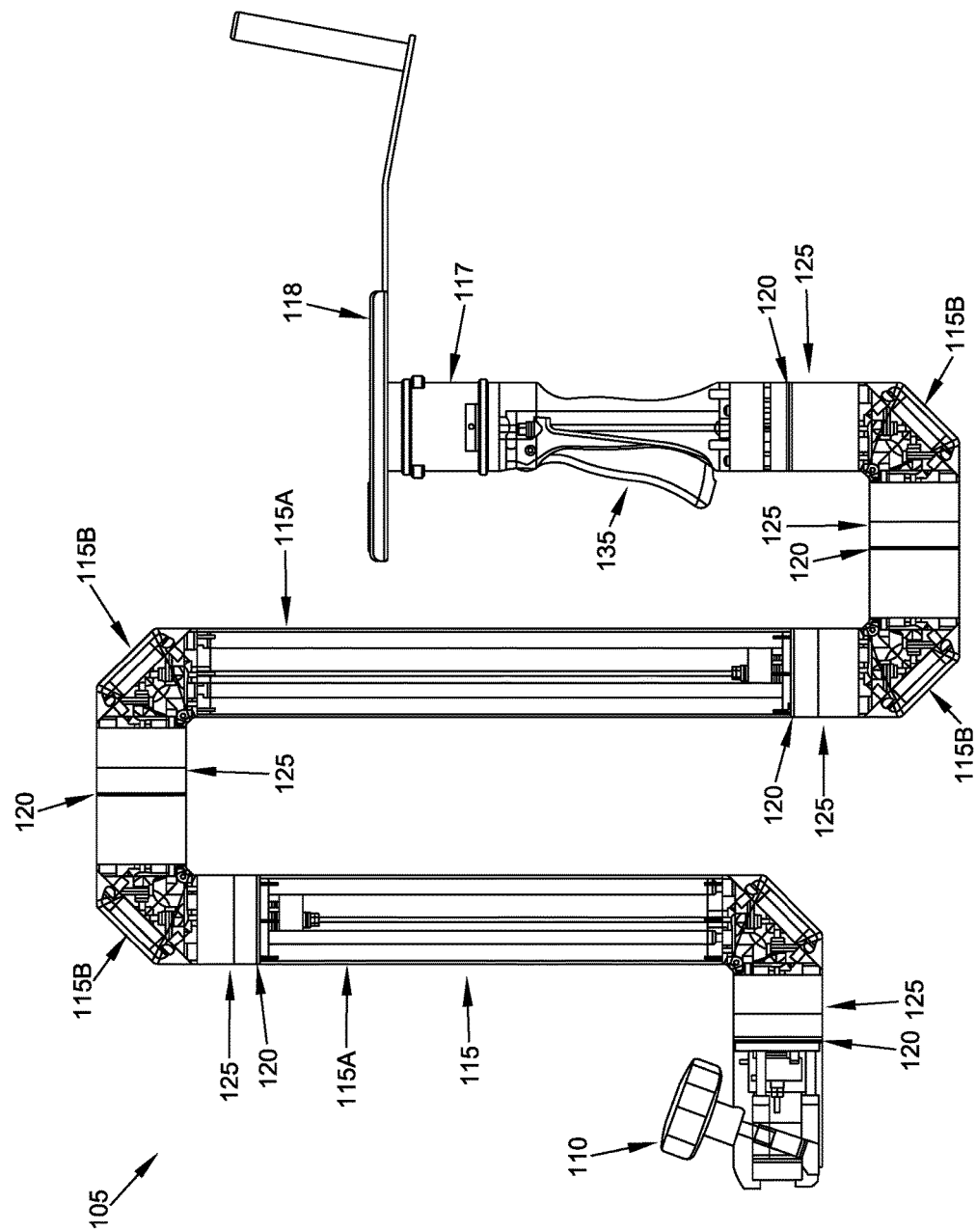

In one preferred form of the present invention, and looking now at FIGS. 1-15, there is provided an adjustable-position limb and/or instrument support arm 5. Adjustable-position support arm 5 comprises a means (e.g., a clamp 10) for attaching adjustable-position support arm 5 to a medical table (such as to the table rail of a medical table), preferably located at one end of the adjustable-position support arm, to which is attached a series of tubular elements 15 rotatably connected to one another in a generally end-to-end fashion, wherein tubular elements 15 are independently rotatable about their longitudinal axes, whereby to provide adjustable-position support arm 5 with a wide range of possible configurations. Adjustable-position support arm 5 also comprises a means (e.g., a mount 17) preferably disposed on the opposing end of the adjustable-position support arm for attaching a working element (e.g., a limb support, an instrument support, etc.—such as the autoclavable sterilizable component 18 shown in FIGS. 11-13) to adjustable-position support arm 5. As will hereinafter be discussed, tubular elements 15 may comprise substantially straight tubular elements 15A and angled tubular elements 15B. Preferably angled tubular elements 15B comprise a right angle configuration so that they have two longitudinal axes set at a right angle to one another.

Straight tubular elements 15A and angled tubular elements 15B are joined to one another at suitable intervals (e.g., straight tubular elements 15A are connected to angled tubular elements 15B, and/or angled tubular elements 15B are connected to other angled tubular elements 15B), whereby to form a series of joints 20 within adjustable-position support arm 5, such that when the various tubular elements 15A, 15B are rotated about their respective longitudinal axes, the configuration of the overall support arm can be adjusted.

At the intersections of the various tubular elements 15A, 15B, locking mechanisms 25 are disposed such that when the locking mechanisms are engaged (i.e., locked), the adjacent tubular elements 15A, 15B are locked against rotation relative to one another. Preferably all of locking mechanisms 25 may be simultaneously engaged (i.e., locked) so that the configuration of the entire assembly of tubular elements 15A, 15B is locked in a particular configuration (i.e., adjustable-position support arm 5 is locked in a particular configuration).

Conversely, when locking mechanisms 25 are disengaged (i.e., unlocked), the adjacent tubular elements 15A, 15B are free to rotate relative to one another. Preferably all of the locking mechanisms 25 may be simultaneously disengaged (i.e., unlocked) so that the entire assembly of tubular elements 15A, 15B is then free to move about its joints 20, i.e., with each tubular element 15A, 15B free to move about its own axis of rotation. In this way, support arm 5 is free to assume a different configuration.

A length of cable 30 (or, alternatively, a series of rods, chains or the like) runs axially through tubular elements 15A, 15B (and through locking mechanisms 25) such that cable 30 can simultaneously move all of the locking mechanisms 25 from an engaged position (i.e., a locked position) to a disengaged position (i.e., an unlocked position) upon activation by the user, i.e., by axial movement of the cable, when a suitable axial force is applied to the cable, e.g., by a lever 35.

It will be appreciated that various bearings, axles, slides, tubular conduits, guides or the like may be provided in or on tubular elements 15A, 15B so as to guide the tubular elements through their previously-described axial rotations.

In one preferred embodiment of the present invention, spring mechanisms 40 are provided within tubular elements 15A, 15B such that locking mechanisms 25 (contained within the tubular elements) are always returned to their engaged position (i.e., their locked position) after tension on cable 30 is relaxed. In other words, in one preferred embodiment of the present invention, locking mechanisms 25 are all normally maintained in their engaged position (i.e., locked position), but they may all be simultaneously moved into their disengaged position (i.g., unlocked position) by applying tension on cable 30, and may thereafter all be returned to their engaged position (i.e., locked position) by relaxing the tension imposed on cable 30, whereupon spring mechanisms 40 return all of locking mechanisms 25 to their engaged position (i.e., locked position).

A release mechanism (e.g., the aforementioned lever 35) is connected to cable 30 so that an operator can (i) manually apply tension to cable 30, whereby to simultaneously release all of locking mechanisms 25, and (ii) thereafter move the assembly of tubular elements 15A, 15B (i.e., adjustable-position support arm 5) into a new configuration. After the assembly of tubular elements 15A, 15B have been moved into their new configuration, the release mechanism (e.g., lever 35) is released, whereby to lock the assembly of tubular elements 15A, 15B (i.e., adjustable-position support arm 5) into its new configuration.

The release mechanism (e.g., lever 35), which operates cable 30 which extends through the series of tubular elements 15A, 15B and selectively releases locking mechanisms 25, may be located anywhere on the adjustable-position support arm 5. In one preferred form of the present invention, the release mechanism (e.g., lever 30) is located on the end of the adjustable-position support arm 5 opposite to the end which is mounted to the medical table.

Figure 1:
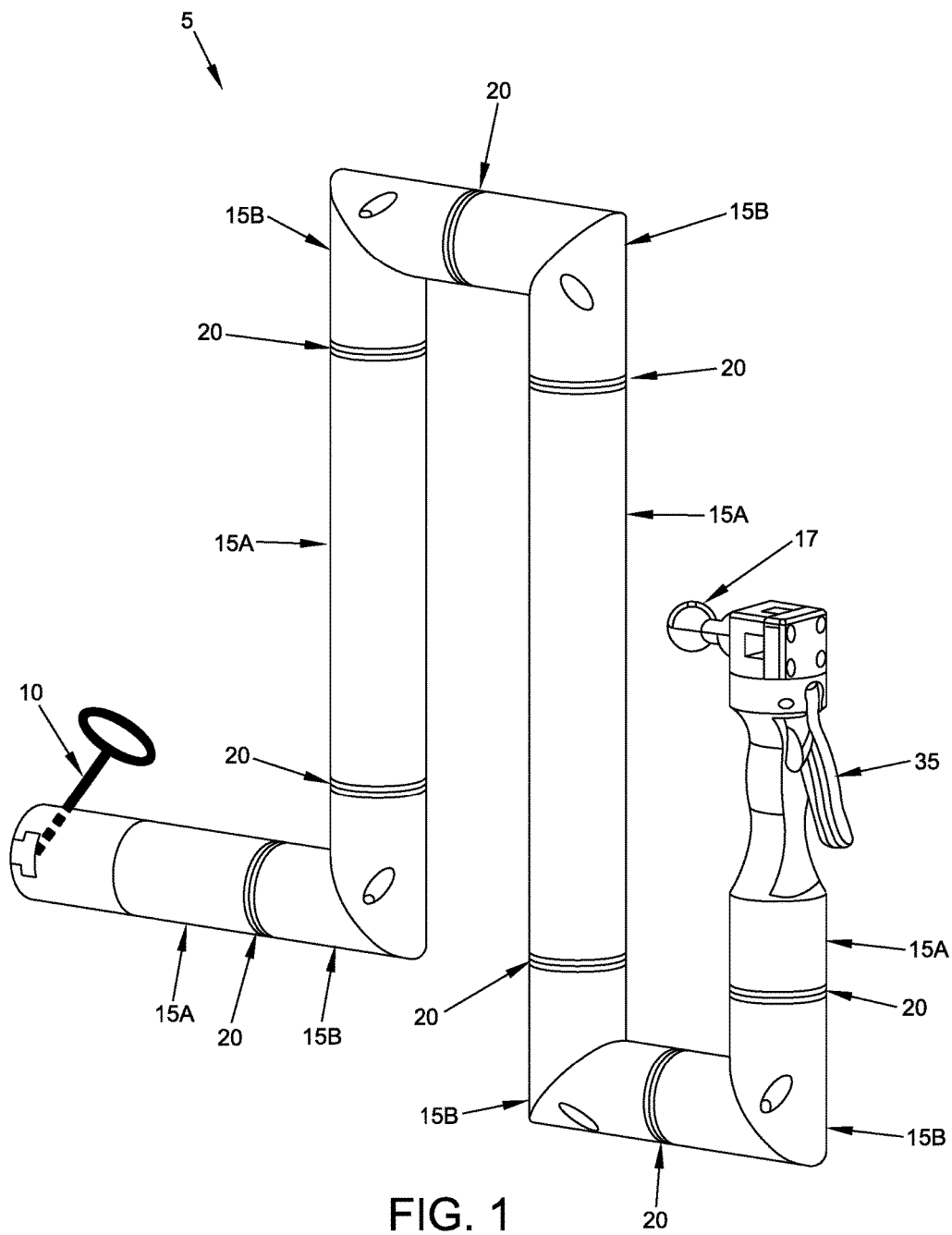
FIGS. 1-10 are schematic views showing one form of an adjustable-position support arm formed in accordance with the present invention.

FIG. 1 shows the overall relationship of the major components of the adjustable-position support arm, consisting of an arrangement of tubular elements 15 (some being straight tubular elements 15A and some being angled tubular elements 15B) connected one to another in end-to-end fashion, with each of the tubular elements 15 being independently rotatable about their longitudinal axes, whereby to permit adjustable-position support arm 5 to assume a variety of configurations.

Figure 2:
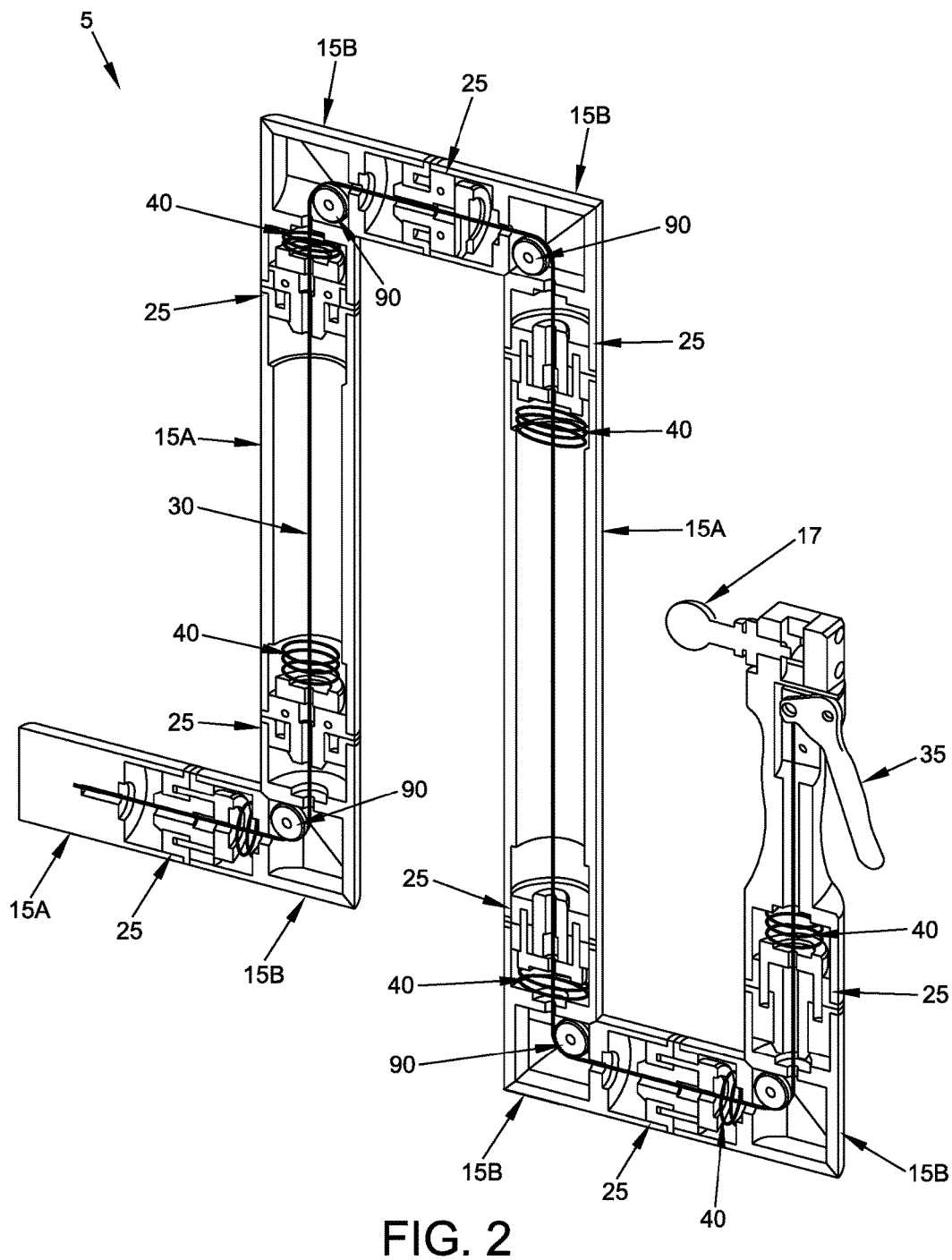

FIG. 2 shows a cross-section of the adjustable-position support arm 5 in FIG. 1. A locking mechanism 25 is placed at the rotatable connection between each of the tubular elements 15. A spring mechanism 40 is positioned at each locking mechanism 25 such that the locking mechanism is maintained in its engaged position (i.e., locked position) at all times, except for when tension is placed on cable 30 (i.e., by activating lever 35), which action disengages (i.e., unlocks) the locking mechanism 25 so that the associated tubular elements 15 can rotate about their longitudinal axes.

Figure 3:
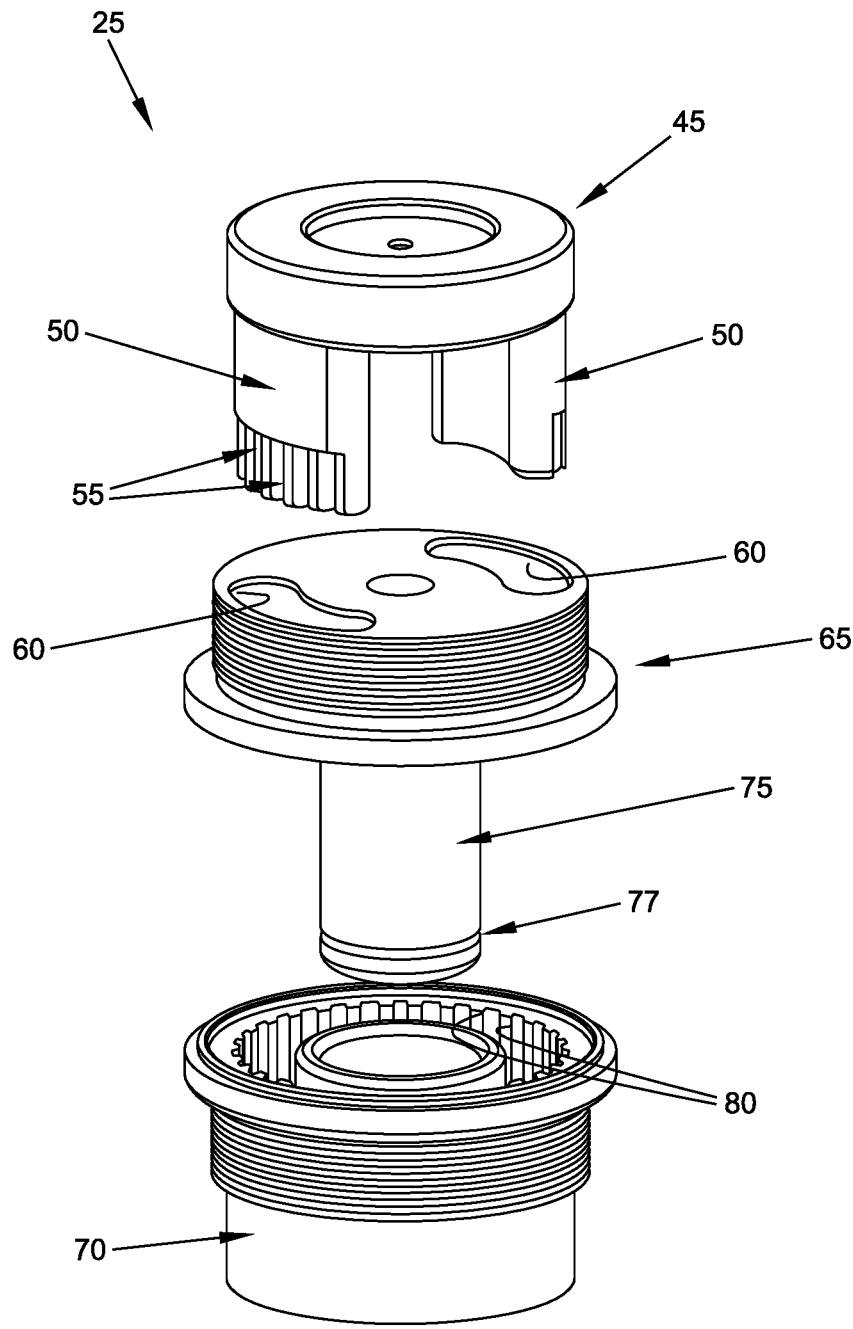

FIG. 3 is an exploded view of one preferred construction for locking mechanism 25. Locking mechanism 25 comprises a male locking gear 45 having two arms 50, with gear-like teeth 55 located at the distal ends of those arms 50. Male locking gear 45 extends through windows 60 formed in a locking guide spindle 65 and selectively locks to a female locking gear 70. By virtue of the fact that the two arms 50 of male locking gear 45 extend through windows 60 formed in locking guide spindle 65, locking guide spindle 65 can rotate only when male locking gear 45 is free to rotate. A shaft portion 75 of locking guide spindle 65 provides an axle about which male locking gear 45 and female locking gear 70 may rotate when they are in their disengaged (i.e., unlocked) condition. In one preferred form of the invention, shaft portion 75 of locking guide spindle 65 comprises a groove 77 for receiving a snap ring (not shown) for holding locking guide spindle 65 to female locking gear 70. Female locking gear 70 comprises gear-like teeth 80 on its inner surface such that teeth 80 of female locking gear 70 mesh and interlock with teeth 55 of male locking gear 45 when male locking gear 45 and female locking gear 70 are slidably moved together to their engaged (i.e., locked) position. When teeth 55 of male locking gear 45 and teeth 80 of female locking gear 70 are engaged with one another, rotational movement of male locking gear 45 and female locking gear 70 relative to one another is prevented (and, by virtue of arms 50 of male locking gear 45 passing through windows 60 in locking guide spindle 65, rotational movement of locking guide spindle 65 and female locking gear 70 relative to one another is also prevented). The aforementioned spring mechanism 40 (FIGS. 2 and 8) normally biases male locking gear 45 into engagement with female locking gear 70.

Locking mechanisms 25 are disposed at the joints 20 between adjacent tubular elements 15. More particularly, locking guide spindle 65 is mounted to one of the adjacent tubular elements 15, and female locking gear 70 is mounted to the other of the adjacent tubular elements 15. When locking mechanism 25 is in its engaged (i.e., locked) position, the adjacent tubular elements 15 are prohibited from rotating relative to one another, and when the locking mechanism 25 is in its disengaged (i.e., unlocked) position, the adjacent tubular elements are allowed to rotate relative to one another.

Figure 4:
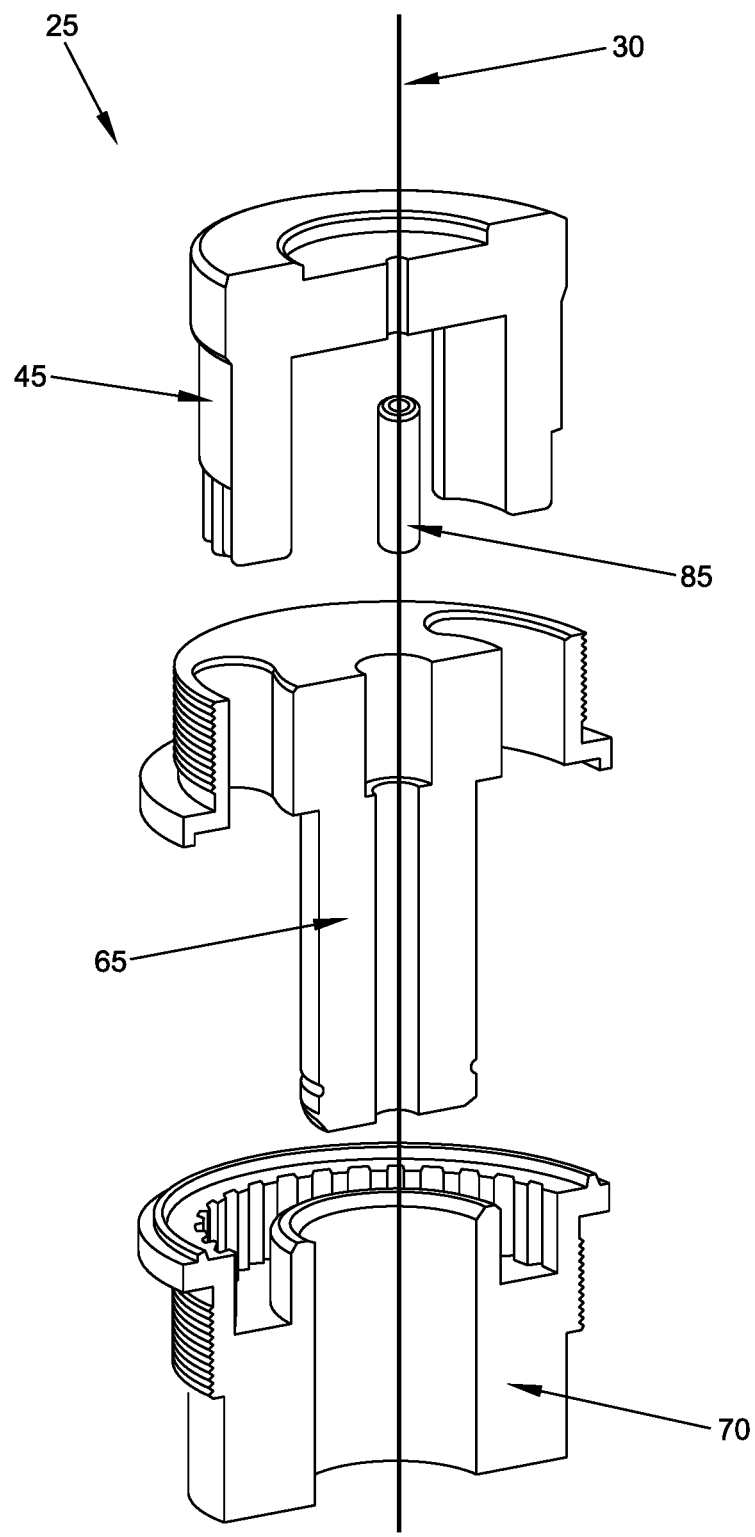

FIG. 4 is an exploded cross-sectional view of the locking mechanism 25 shown in FIG. 3. Cable 30 runs through the locking mechanism 25, with a release node 85 permanently attached to cable 30 between locking guide spindle 65 and male locking gear 45, such that when cable 30 is pulled upward (from the frame of reference shown in FIG. 4), release node 85 contacts the underside of male locking gear 45 and pulls the male locking gear out of engagement with female locking gear 70, thereby disengaging (i.e., unlocking) the locking mechanism 25 (i.e., allowing locking guide spindle 65 and female locking gear 70 to rotate independently of one another, whereby to allow their respective associated tubular elements 15 to rotate relative to one another).

Figure 5:
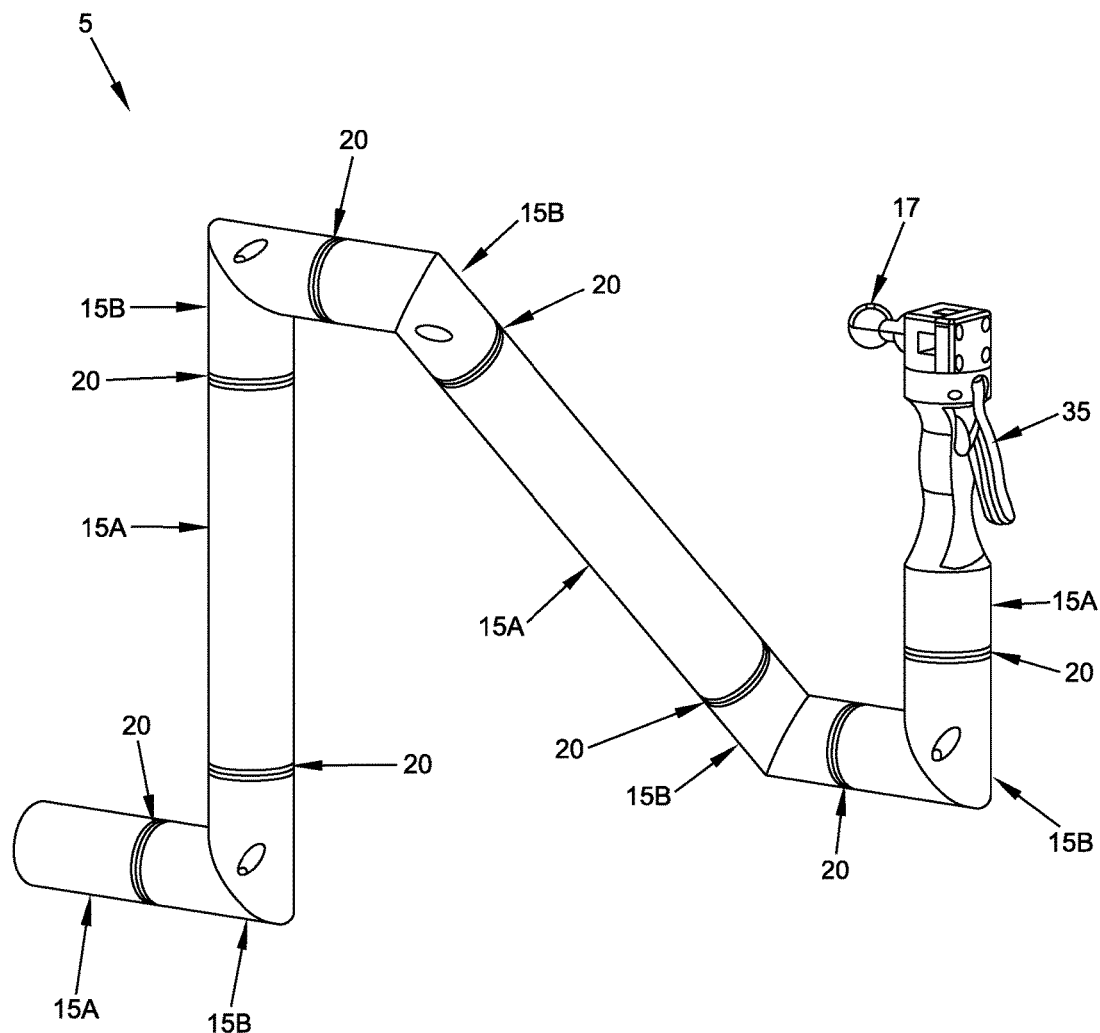
Figure 6:
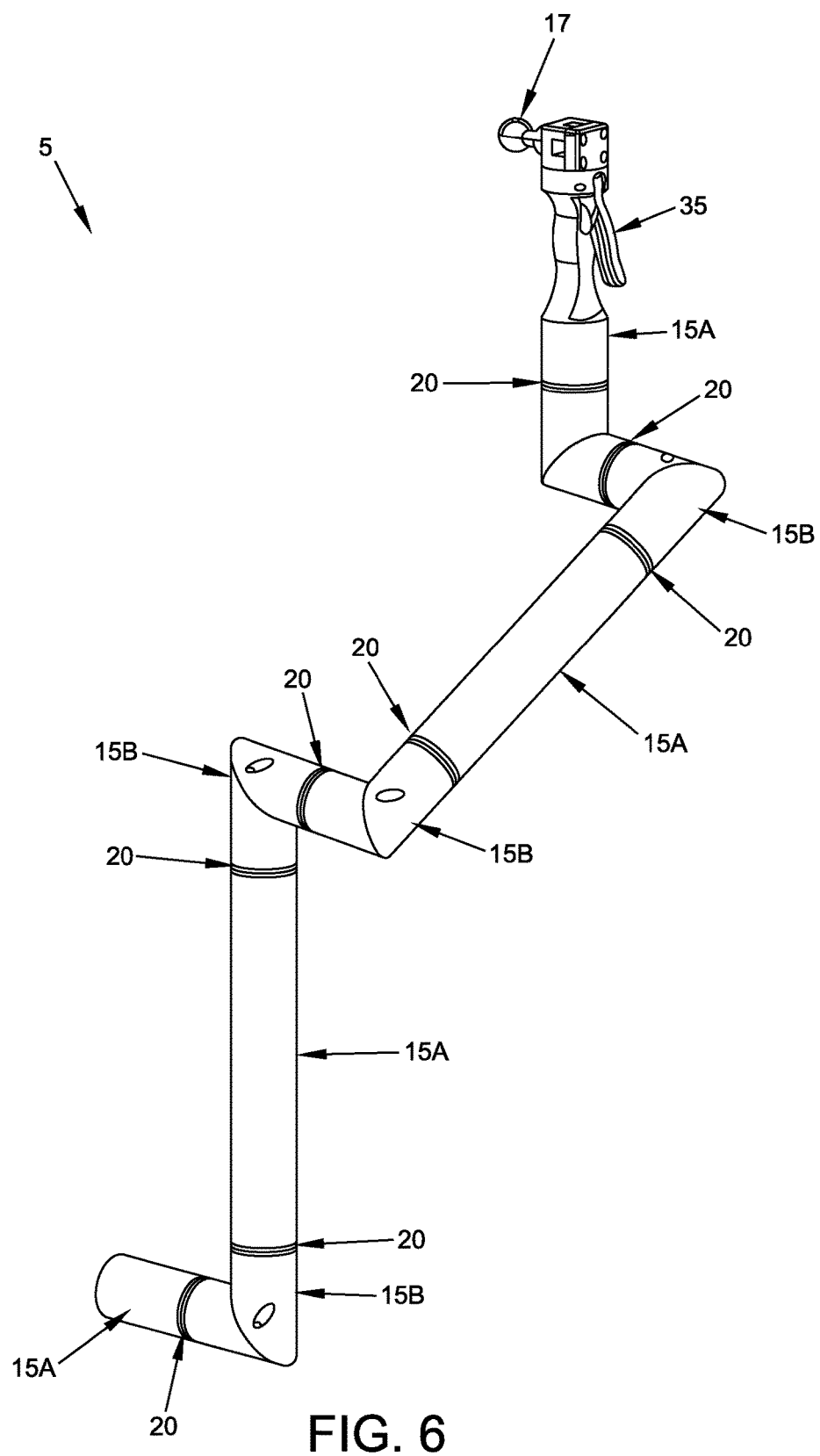

FIGS. 5 and 6 show how the various tubular elements 15 of adjustable-position support arm 5 may be reconfigured when the gears of the locking mechanisms 25 are released relative to each other. More particularly, FIG. 5 shows support arm 5 after being released and re-locked in a configuration which is different from the configuration shown in FIG. 1. FIG. 6 shows the support arm 5 of FIG. 5 reconfigured into still another configuration. In other words, by pulling on cable 30 extending through adjustable-position support arm 5, the various release nodes 85 positioned on cable 30 are simultaneously moved against the various male locking gears 45 of locking mechanisms 25, whereby to simultaneously release all of the locking mechanisms contained within the adjustable-position support arm, thereby allowing the support arm to be reconfigured by the user.

In the adjustable-position support arm 5 shown in FIGS. 1-15, there are 24 distinct positions for each locking mechanism 25 (determined by the number of teeth 55, 80 provided on male locking gear 45 and female locking gear 70, respectively, in the locking mechanism), and 8 different locking mechanisms 25, thereby resulting in $1.1 \times 10^{11}$ possible positions for adjustable-position support arm 5. Obviously, additional distinct locking positions (provided by utilizing more teeth for each locking gear 45, 70) result in more possible positions for adjustable-position support arm 5. Furthermore, utilizing additional rotatably-jointed tubular elements 15 within the support arm (each spanned by a locking mechanism 25) will also result in more possible positions for adjustable-position support arm 5. Alternatively, less teeth may be used in each locking mechanism 25, and/or less locking mechanisms may be used in the adjustable-position support arm 5. Thus it should be appreciated that the particular exemplary construction disclosed herein is not intended to limit the invention in any way.

It is, therefore, possible to position support arm 5 so as to hold a limb and/or instrument precisely in substantially any configuration useful in a medical procedure.

Figure 7:
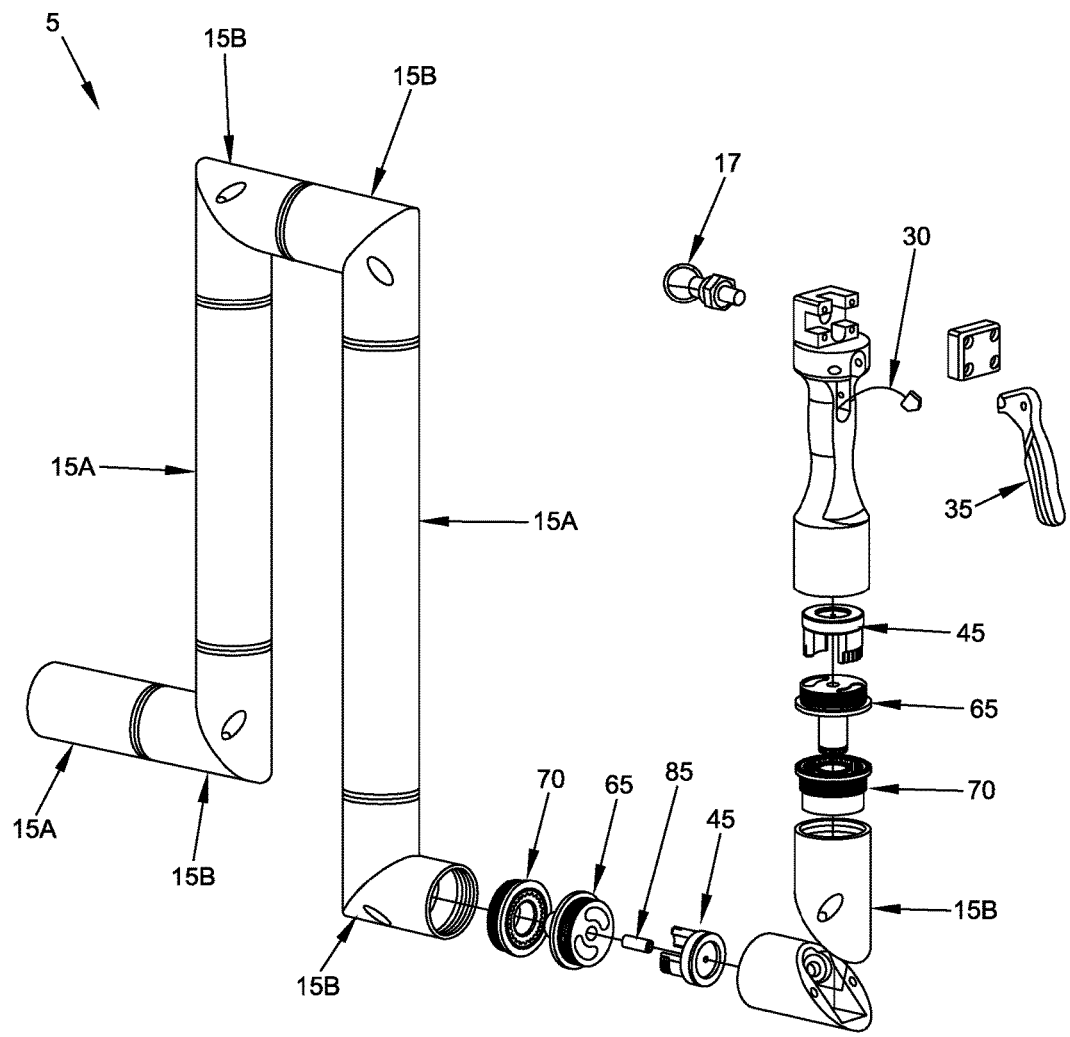

FIG. 7 shows the functional components of adjustable-position support arm 5 in relation to each other in a partially-exploded perspective view.

Figure 8:
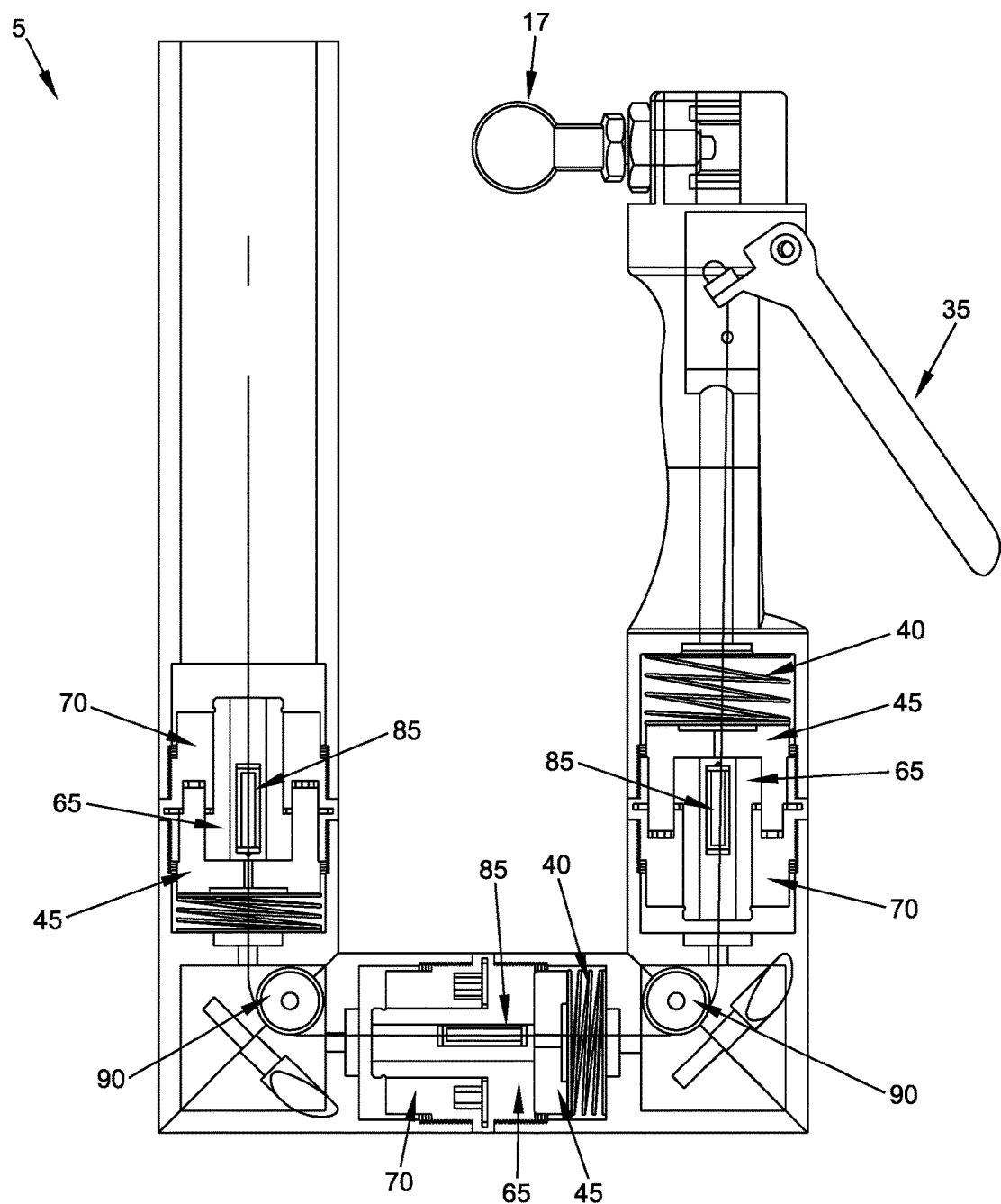

FIG. 8 shows a partial sectional view of a portion of adjustable-position support arm 5, including the releasing lever 35. In this view, locking mechanisms 25 (each consisting of a male locking gear 45, locking guide spindle 65 and female locking gear 70) are shown in their engaged (i.e., locked) position. Note that inasmuch as teeth 55 of male locking gear 45 are engaged with teeth 80 of female locking gear 70, the tubular elements 15 (to which locking guide spindle 65 and female locking gear 70 are attached) are prohibited from rotating about their respective longitudinal axes.

Figure 9:
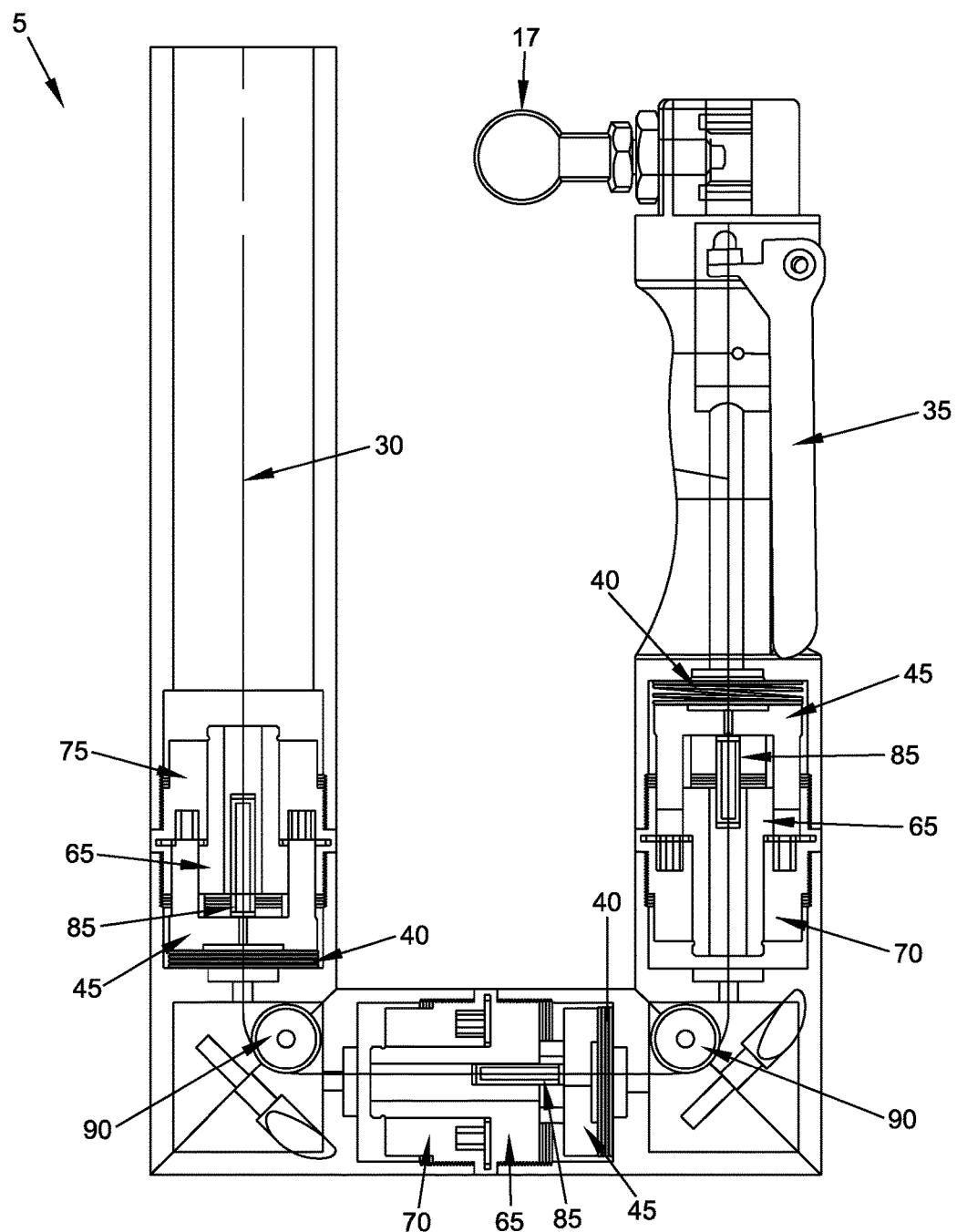

FIG. 9 is a partial sectional view similar to that of FIG. 8, except that in FIG. 9, lever 35 is in its activated position, pulling cable 30 and thereby bringing all of the cable nodes 85 into contact with all of the male locking gears 45 and pulling those male locking gears out of engagement with their counterpart female locking gears 70. Thus, in this figure, lever 35 has moved cable 30, which has moved all of the cable nodes 85, which have urged all of the male locking gears 45 so as to overcome the bias of the aforementioned spring mechanisms 40, whereby to separate male locking gears 45 and female locking gears 70 and thereby place all of the locking mechanisms 25 in their disengaged (i.e., unlocked) positions. Note that in this state, female locking gears 70 are free to rotate about their respective locking guide spindles 65 and the tubular elements 15 to which the locking guide spindles 65 and female locking gears 70 are attached are then free to rotate about their respective longitudinal axes.

Thus it will be seen that the overall device comprises a series of tubular elements 15 which are connected to one another via a series of joints 20, with locking mechanisms 25 being disposed at each of those joints. At each joint 20, the locking guide spindle 65 is secured to one of the adjacent tubular elements 15 and the female locking gear 70 is secured to the other of the adjacent tubular elements 15. As a result of this construction, when the locking mechanism 25 is in its engaged (i.e., locked) condition, the two tubular elements 15 of a given joint 20 are locked to one another so that the tubular elements are held against rotation; however, when the locking mechanism 25 is in its disengaged (i.e., unlocked) condition, the two tubular elements 15 of a given joint 20 are free to rotate relative to one another. Each of the locking mechanisms 25 is normally held in its engaged (i.e., locked) condition by spring mechanisms 40, however, the bias of these spring mechanisms can be overcome by moving cable 30. More particularly, the movement of cable 30 causes the release nodes 85 mounted on the cable to simultaneously force all of the male locking gears 45 to disengage from all of the female locking gears 70, whereby to simultaneously release all of the locking mechanisms 25, and thereby allow the tubular elements 15 to rotate at each joint 20, whereby to allow support arm 5 to be reconfigured.

As shown in both FIGS. 8 and 9, a bearing element (e.g., a pulley 90) is preferably incorporated in each of the angled tubular elements 15B, at the intersection of the two longitudinal axes of the angled tubular element 15B, so that cable 30 passes smoothly through the angled tubular element 15B, without kinking or pulling against sharp edges or corners and with a minimum of friction, so as to prevent damage the cable.

Figure 10:
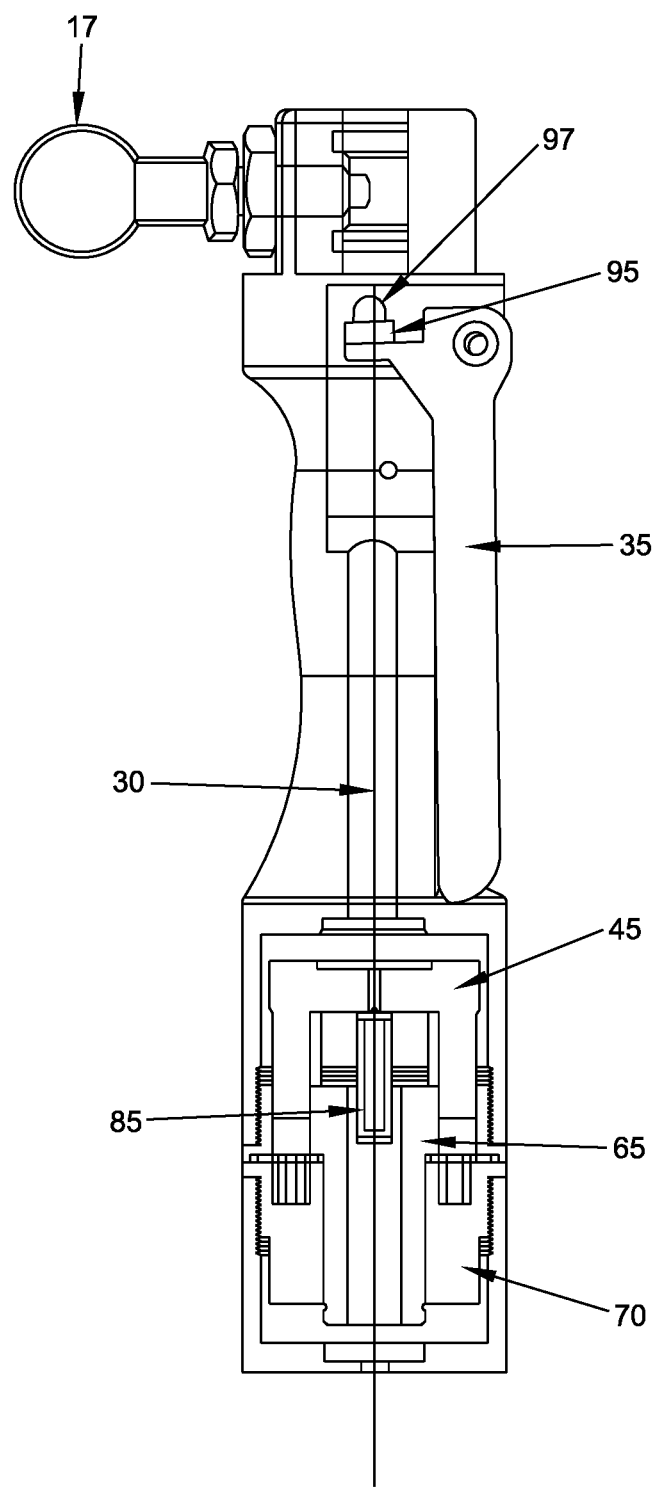

FIG. 10 is a partial sectional view of the portion of adjustable-position support arm 5 carrying lever 35. In one preferred form of the invention, lever 35 comprises a bearing 95 which engages a ball 97 set at the head of cable 30. Ball 97 turns freely on bearing 95 such that any twisting of cable 30 caused by the rotation of the tubular elements 15 is relieved at the head of cable 30.

FIGS. 11-15 show a modified form of the present invention. In this form of the invention, the nodes 85 for releasing the locking mechanisms 25 are releasably mounted to cable 30. More particularly, in this form of the invention, each of the nodes 85 has a longitudinal bore 98 formed therein for receiving the cable, and a crossbore 99 intersecting the longitudinal bore 98 for receiving a set screw (not shown) for releasably securing node 85 to cable 30.

Rod-Based Adjustable-Position Support Arm

Looking next at FIGS. 16-36, there is shown another adjustable-position support arm 105 also formed in accordance with the present invention.

Adjustable-position support arm 105 is generally similar to the aforementioned adjustable-position support arm 5, in the sense that it comprises: (i) a means (e.g., a clamp 110) for attaching adjustable-position support arm 105 to a medical table (see, for example, FIGS. 16-20); (ii) a series of tubular elements 115 (e.g., straight tubular elements 115A and angled tubular elements 115B) rotatably connected to one another at a series of joints 120, whereby to provide support arm 105 with a wide range of possible configurations (see, for example, FIGS. 16-18); (iii) a means (e.g., a mount 117) preferably disposed on the opposing end of the support arm for attaching a working element (e.g., a limb support, an instrument support, etc.—such as the autoclavable sterilizable component 118) to the opposing end of the adjustable-position support arm (see, for example, FIGS. 16-20); (iv) locking mechanisms 125 located at each of the joints 120 for prohibiting rotation about the joints 120, whereby to lock adjustable-position support arm 105 in a particular configuration (see, for example, FIGS. 18-20); and (v) an actuator 130 connected to a lever 135 for selectively, simultaneously disengaging (i.e., unlocking) all of the locking mechanisms 125, whereby to permit tubular elements 115 to rotate about their joints 120 and thereby allow support arm 105 to be re-configured into another configuration.

However, in this form of the invention, among other things: (i) the aforementioned locking mechanism 25 of adjustable-position support arm 5 has been replaced by a different locking mechanism 125 in adjustable-position support arm 105 (see, for example, FIGS. 18-20); and (ii) the aforementioned actuator cable 30 of adjustable-position support arm 5 has been replaced by a different actuator 130 in adjustable-position support arm 105.

Figure 19:
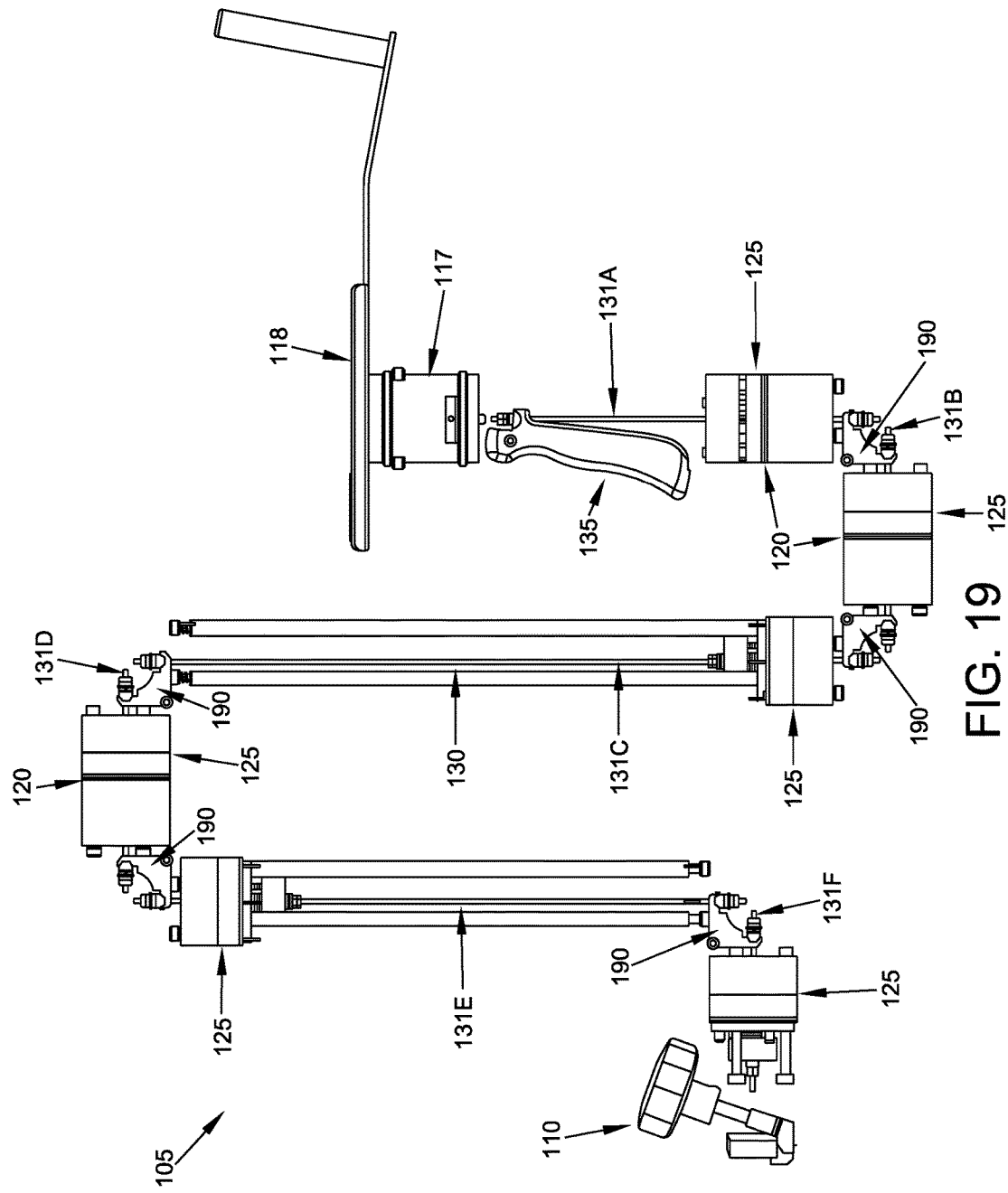
Figure 20:
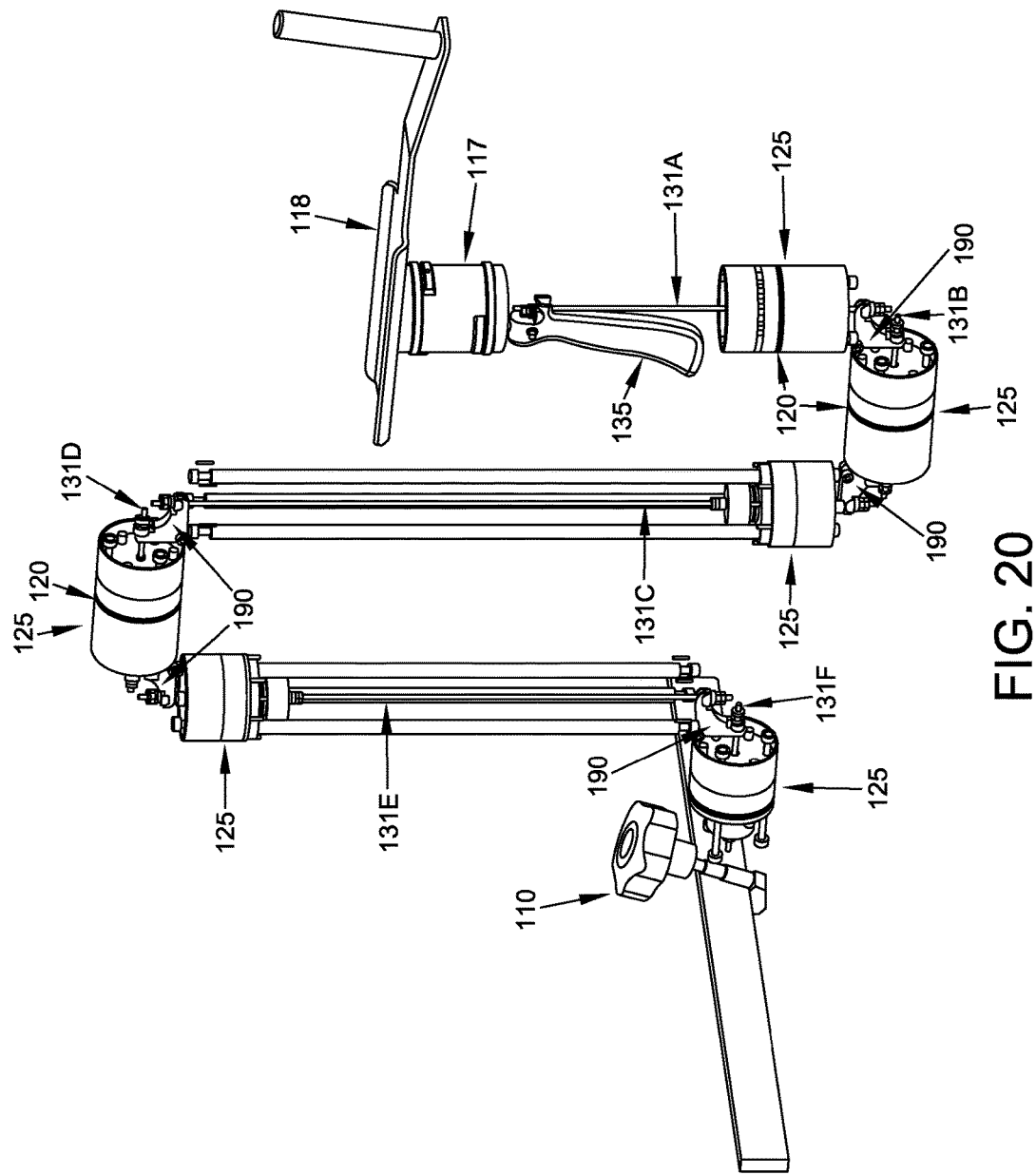
Figure 21:
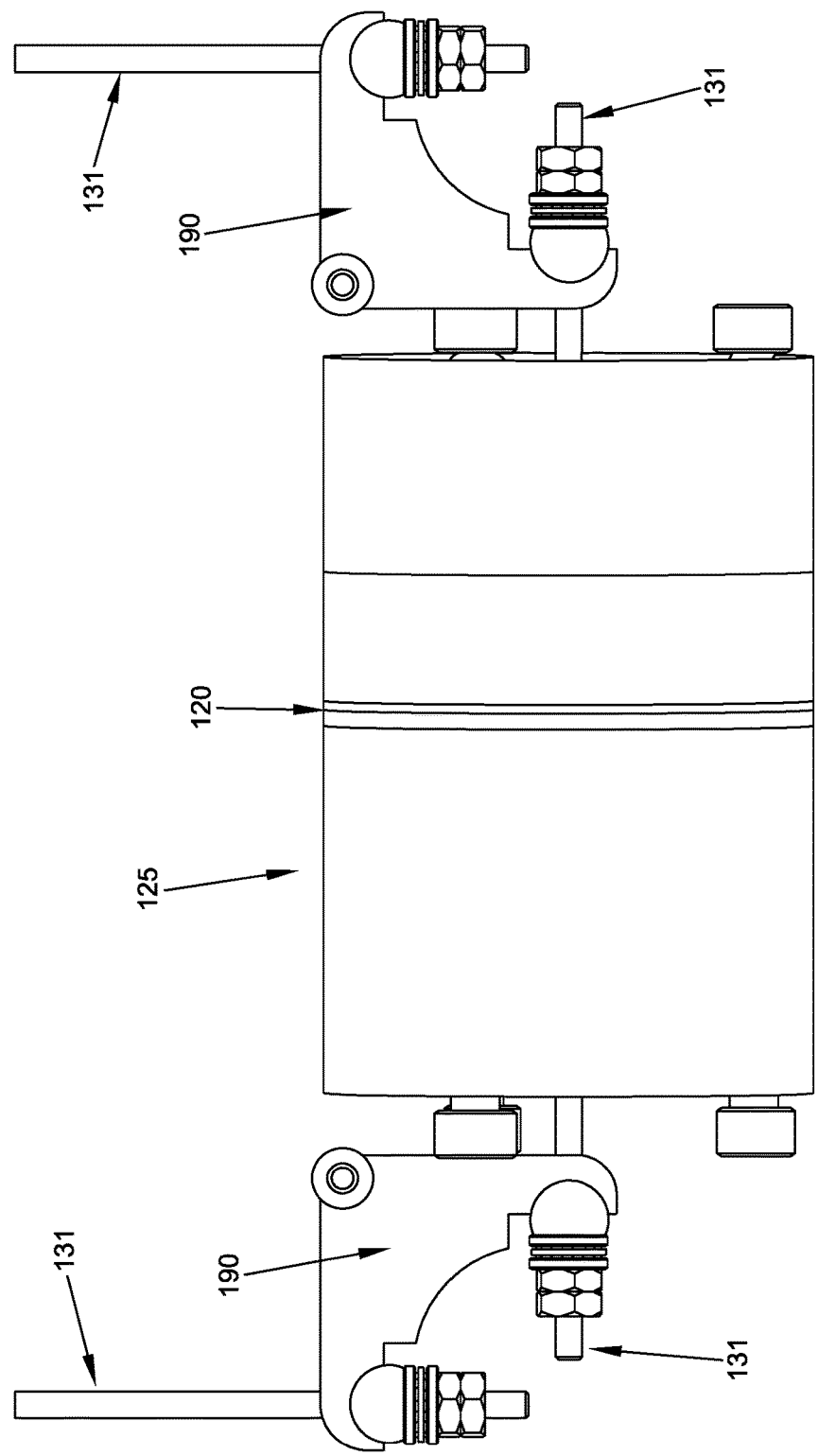
Figure 22:
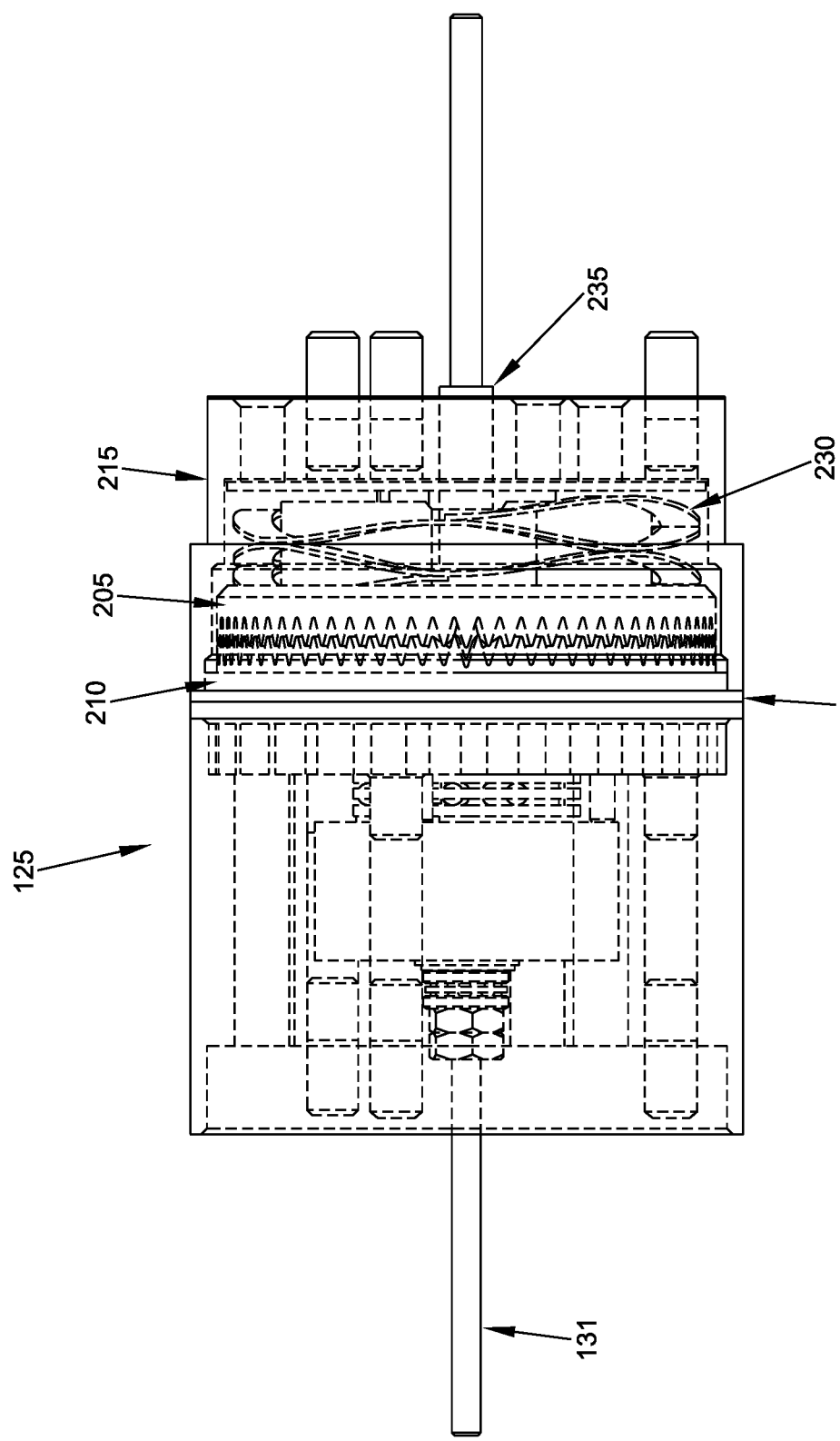
Figure 23:
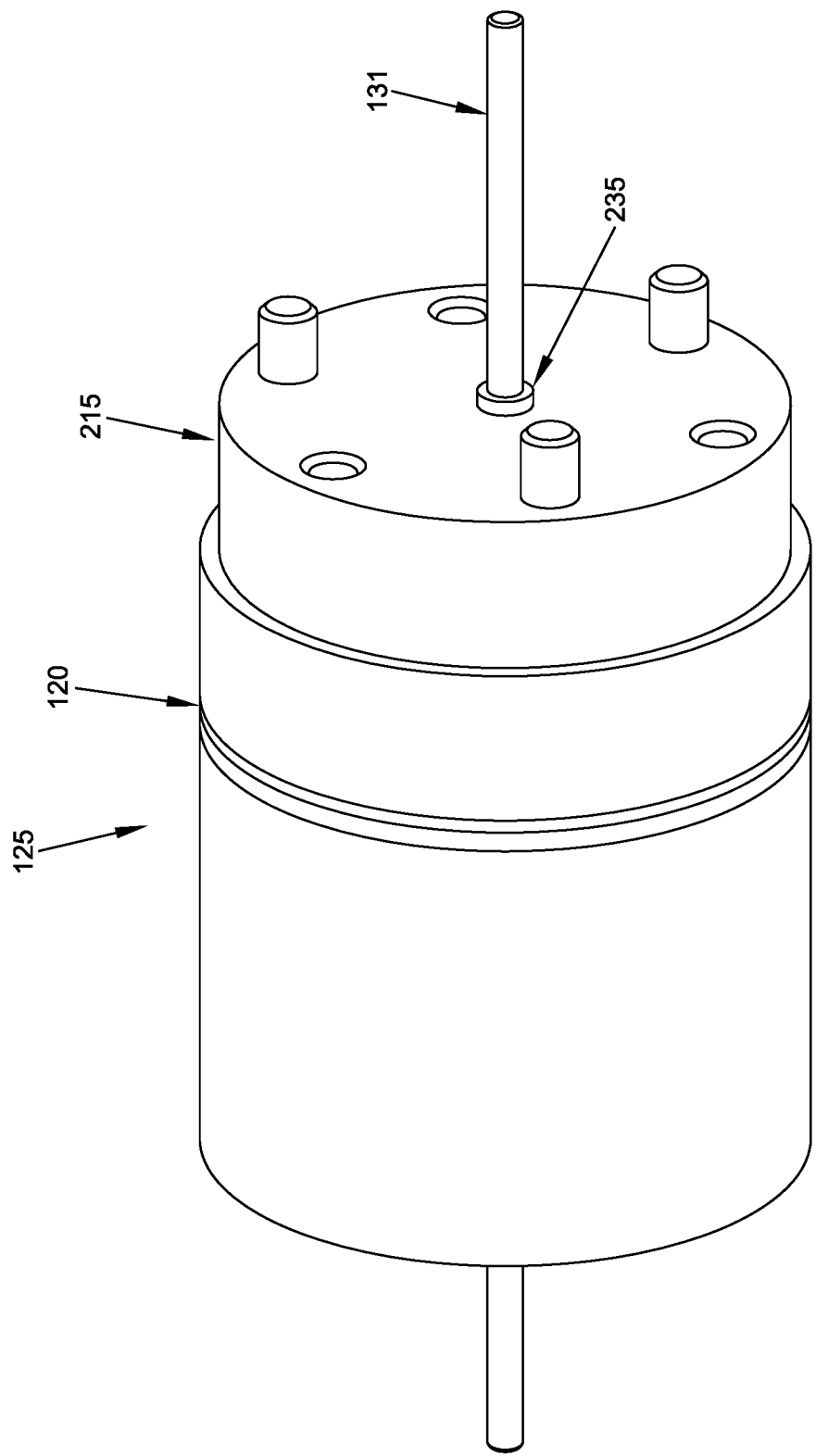
Figure 24:
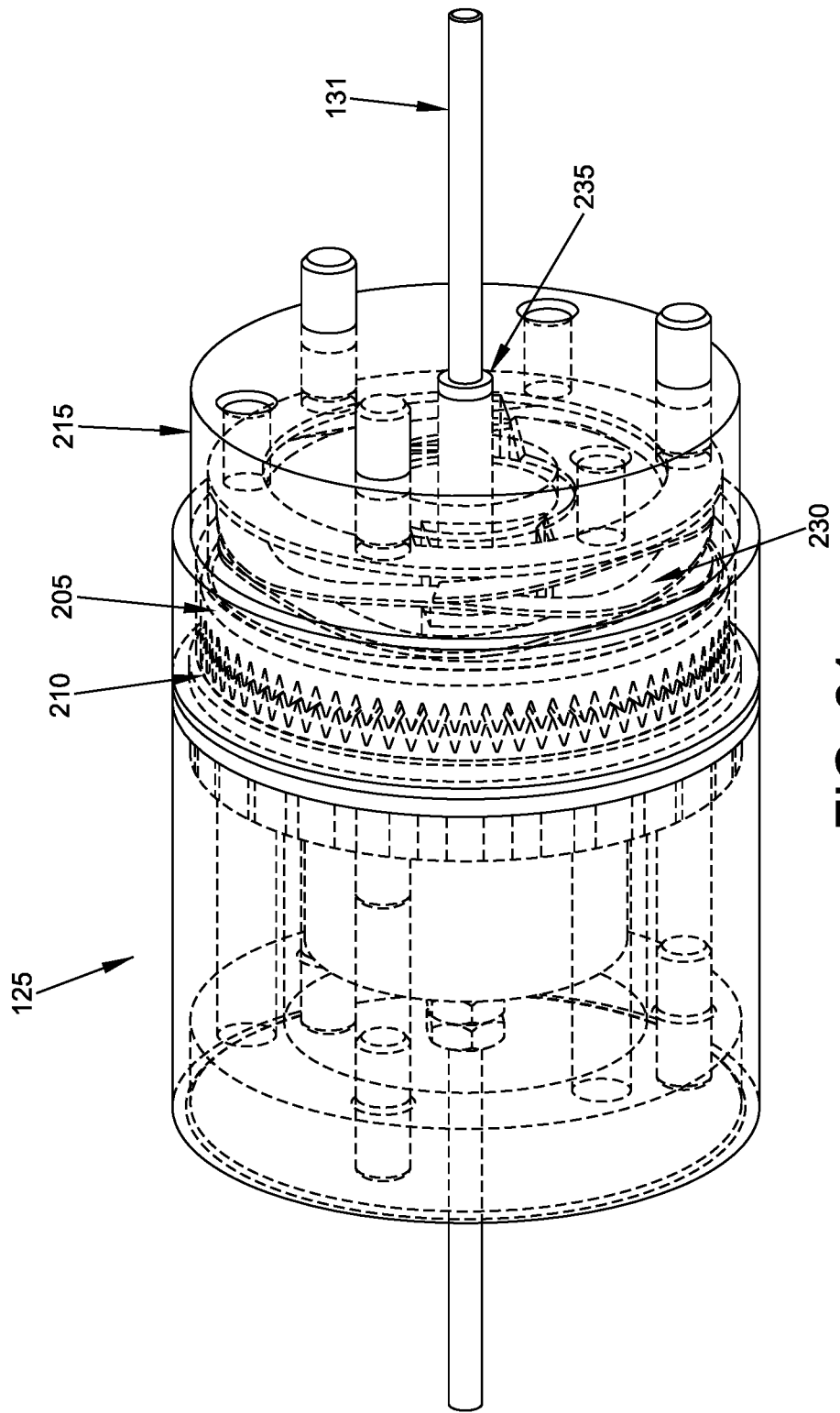
Figure 25:
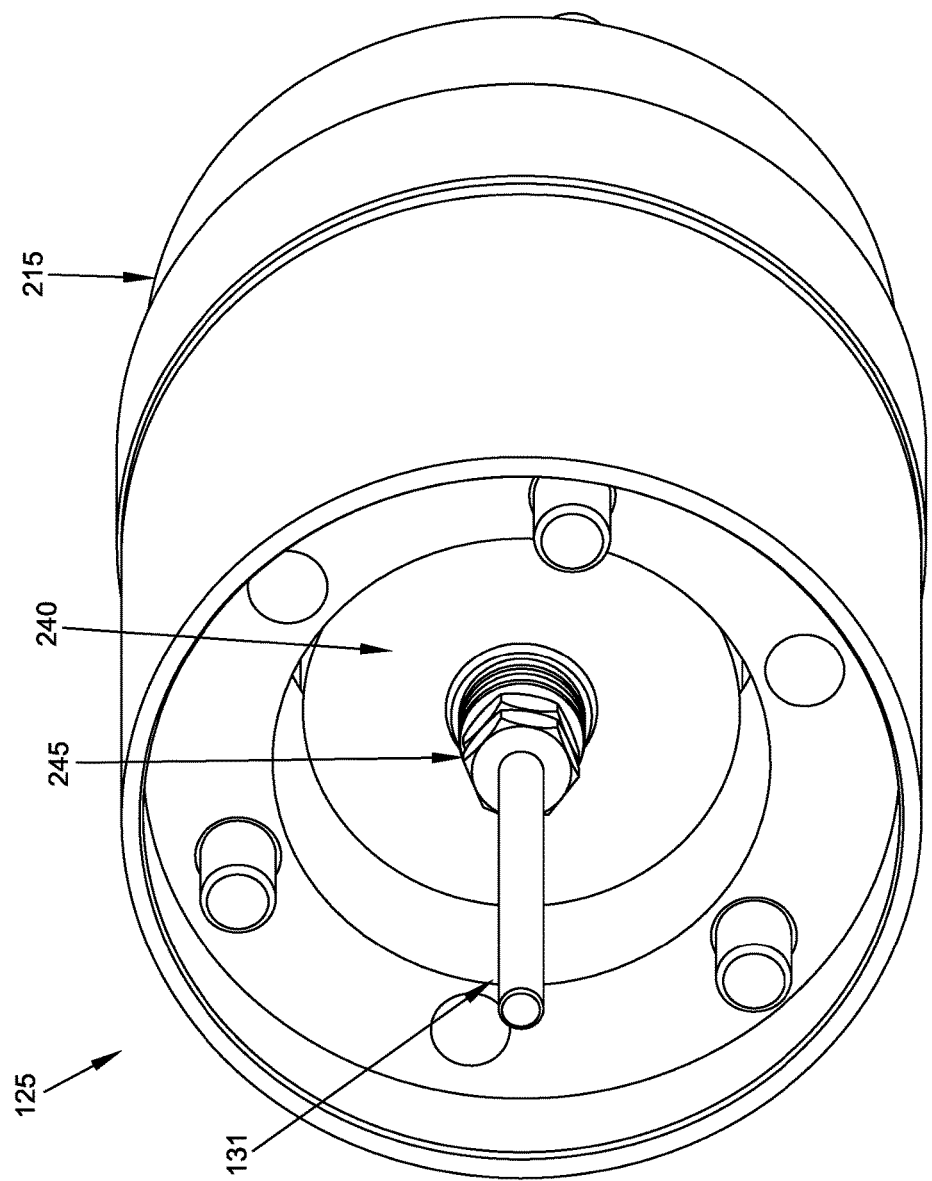
Figure 26:
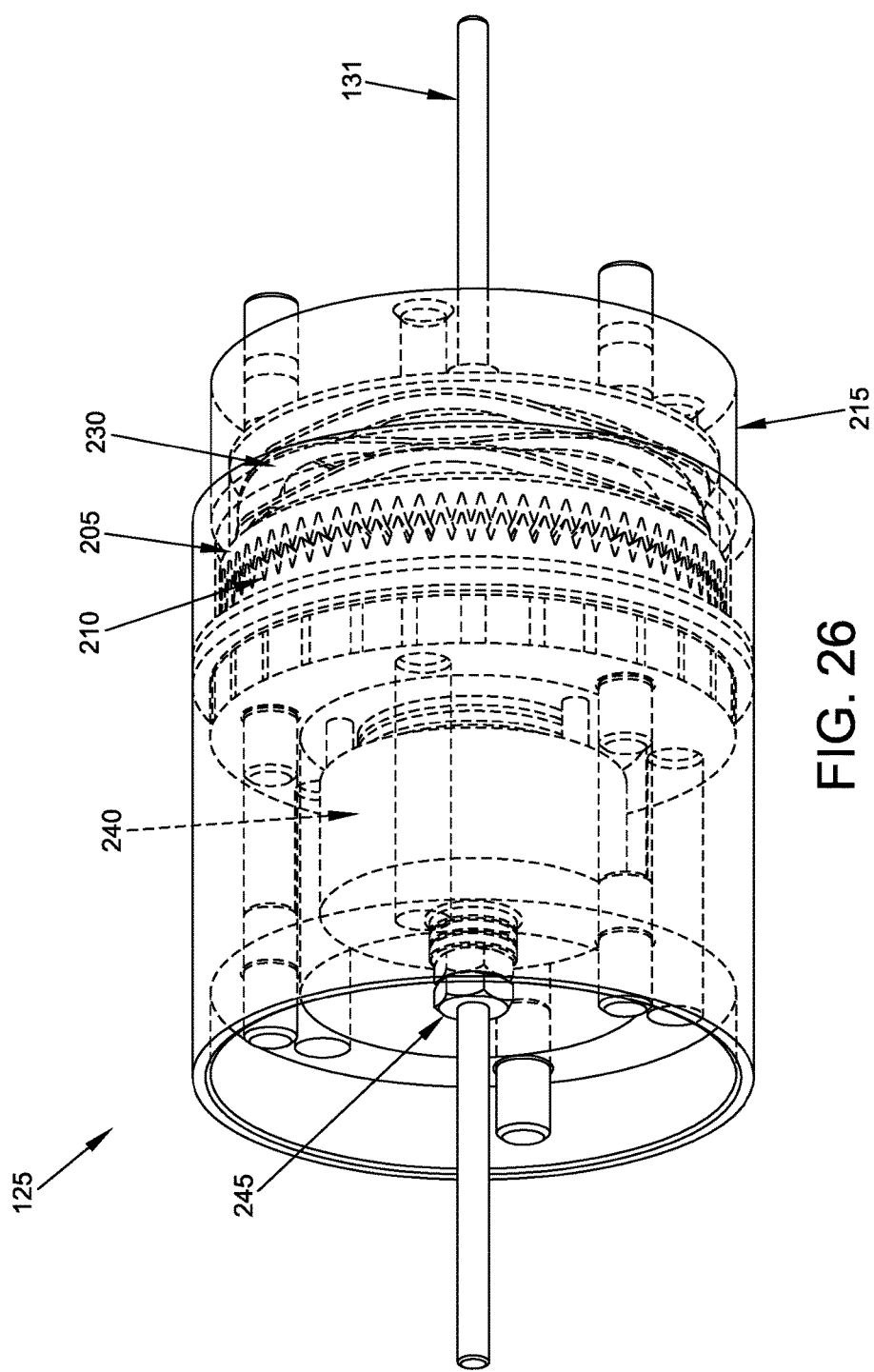
Figure 27:
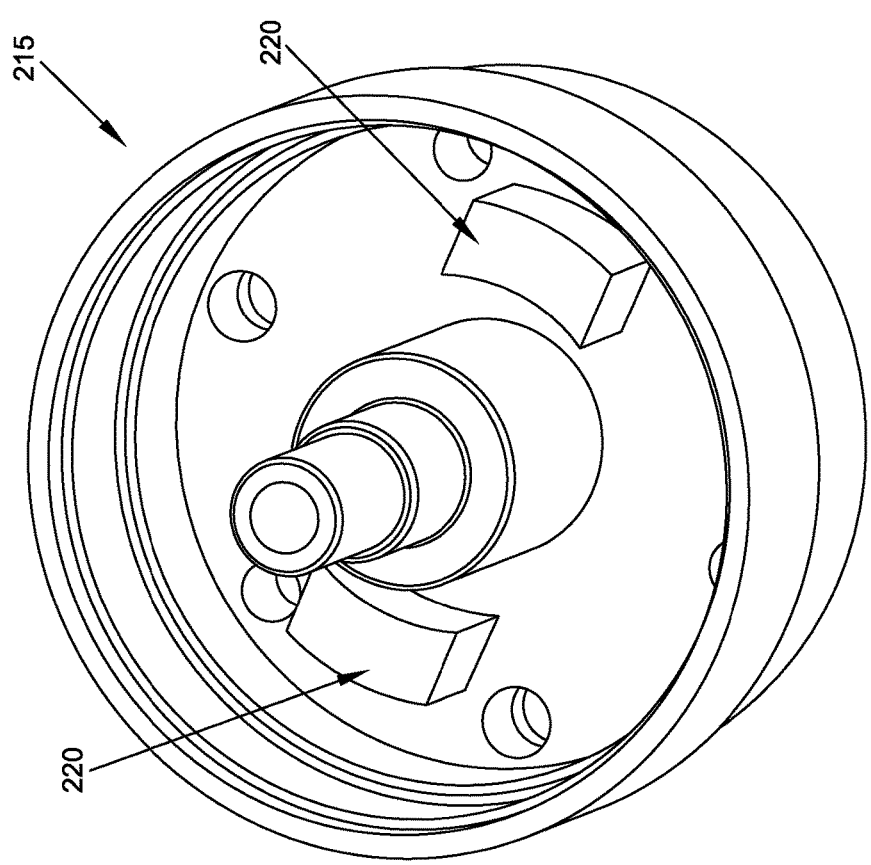

More particularly, in this form of the invention, the actuator 130 of adjustable-position support arm 105 comprises a rod linkage comprising a series of rods 131A, 131B, 131C, etc. which extend through tubular elements 115 and locking mechanisms 125 (see, for example, FIGS. 18-20) and which are connected together at their intersections by pivot arms 190 which are rotatably mounted within angled tubular elements 115B (see, for example, FIGS. 19 and 20). Thus, in this form of the invention, actuator 130 of adjustable-position support arm 105 comprises a rod linkage comprising rods 131A, 131B, 131C, etc. connected together at their intersections by pivot arms 190. And in this form of the invention, one end of the rod linkage of actuator 130 is connected to the lever 135 mounted on adjustable-position support arm 105, whereby to allow the user to apply "pull" to the rod linkage, and one rod 131 extends through each locking mechanism 125, whereby that rod of the rod linkage of actuator 130 can be used to actuate the locking mechanism which it extends through, as will hereinafter be discussed.

Figure 28:
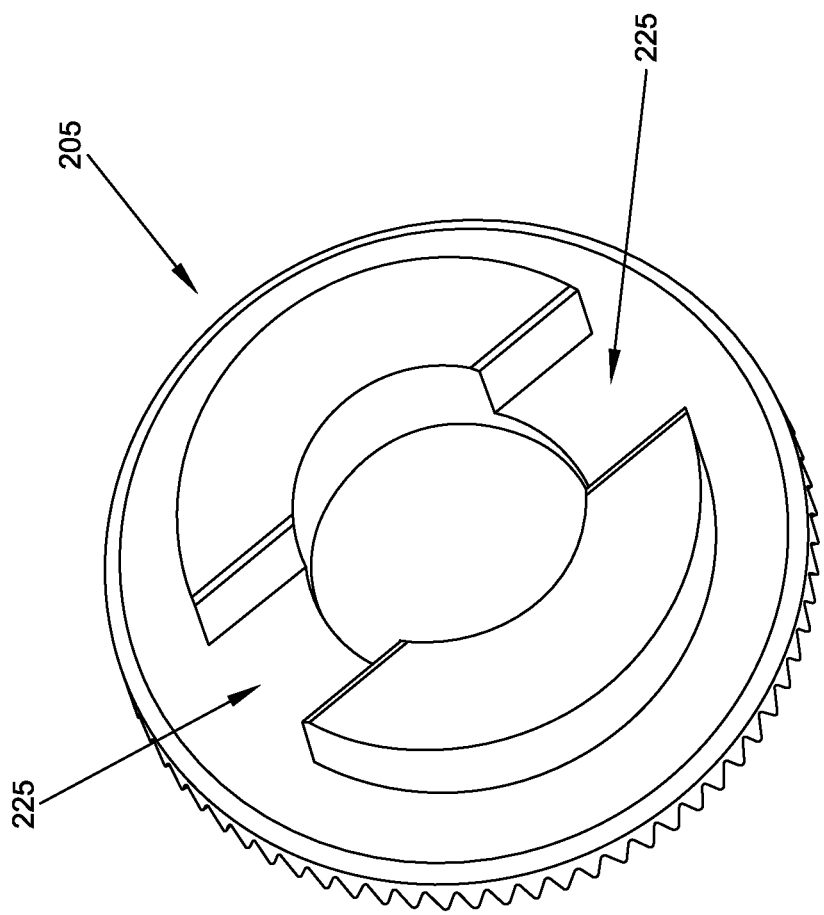
Figure 29:
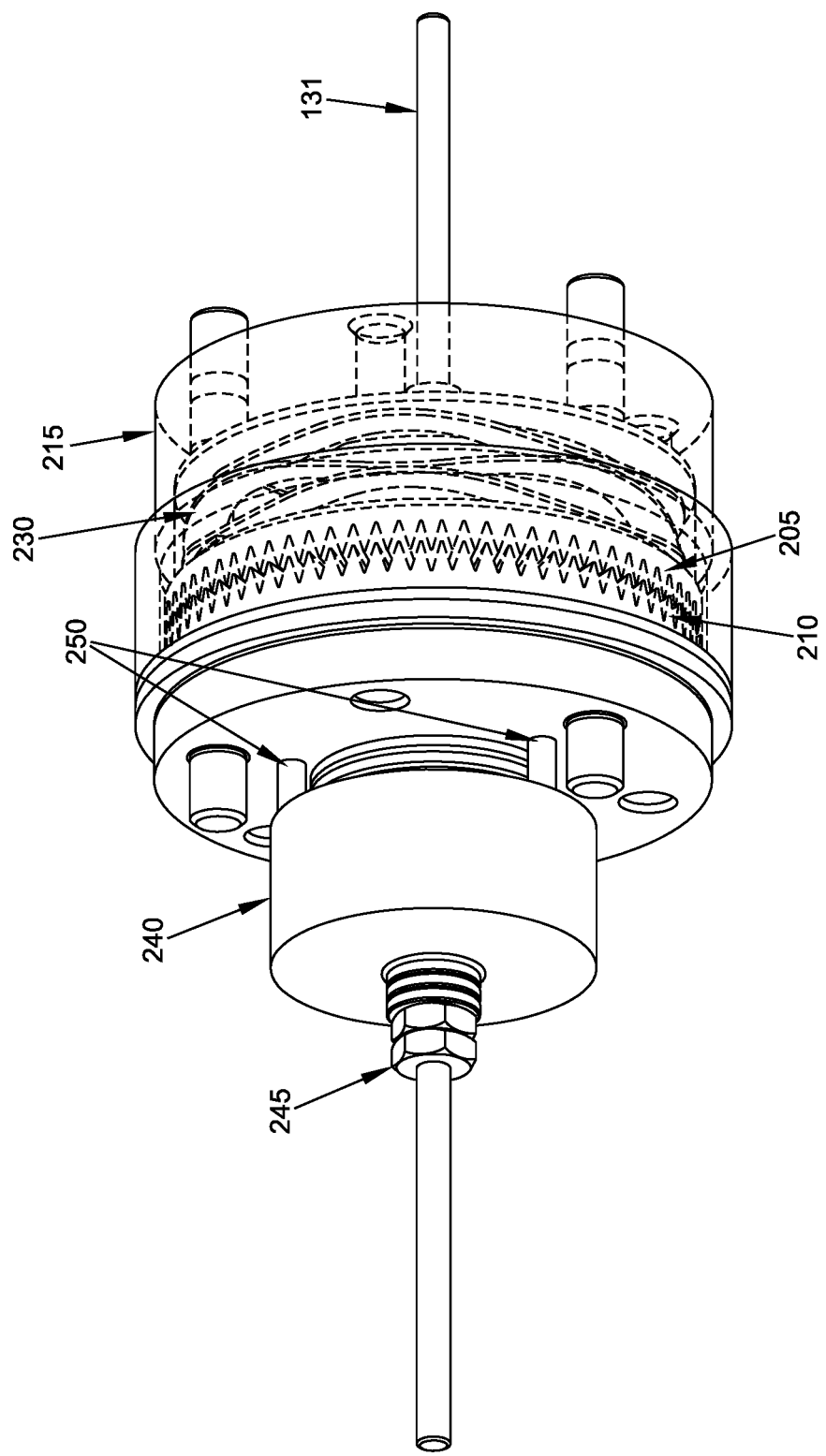
Figure 30:
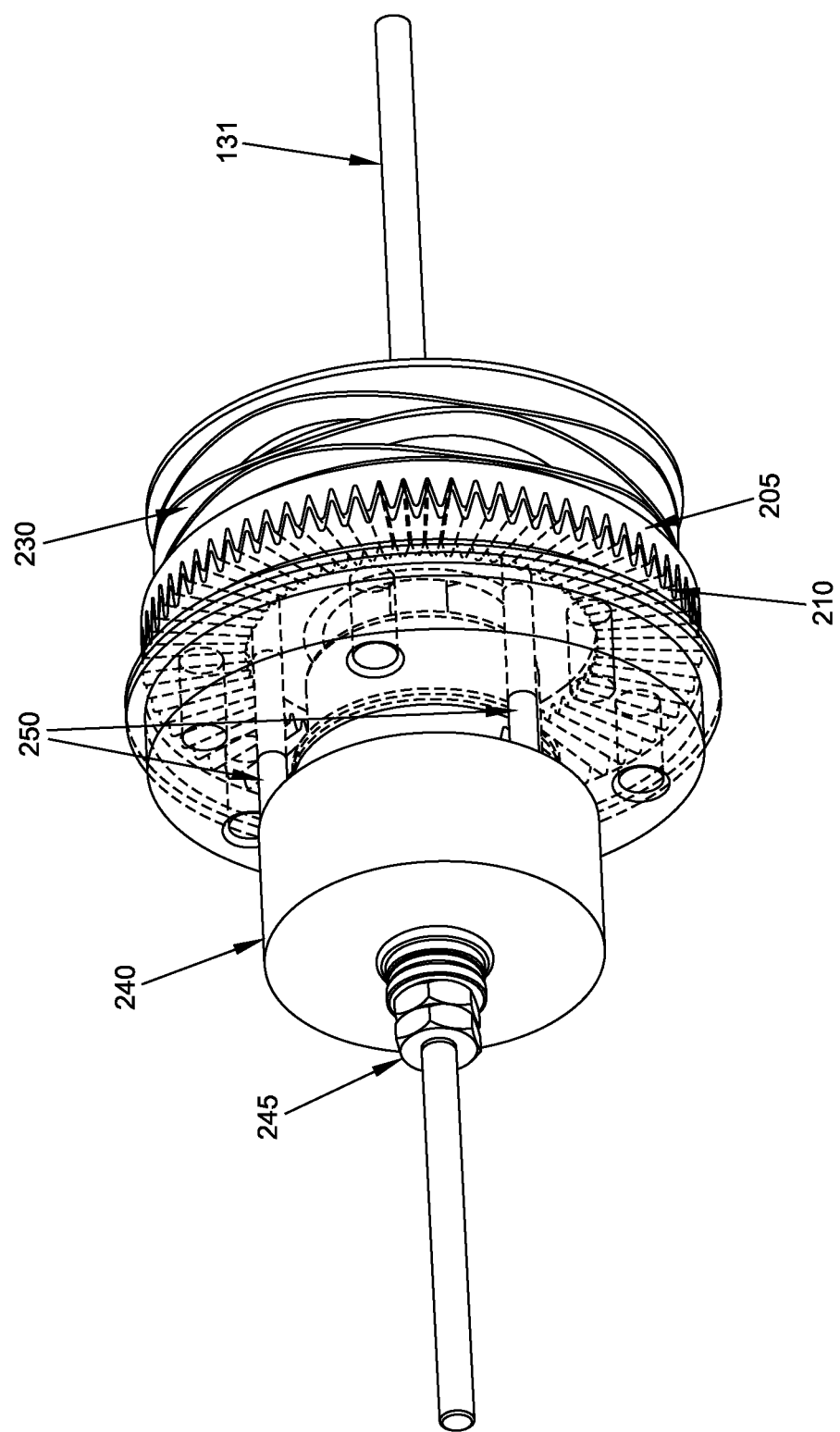
Figure 31:
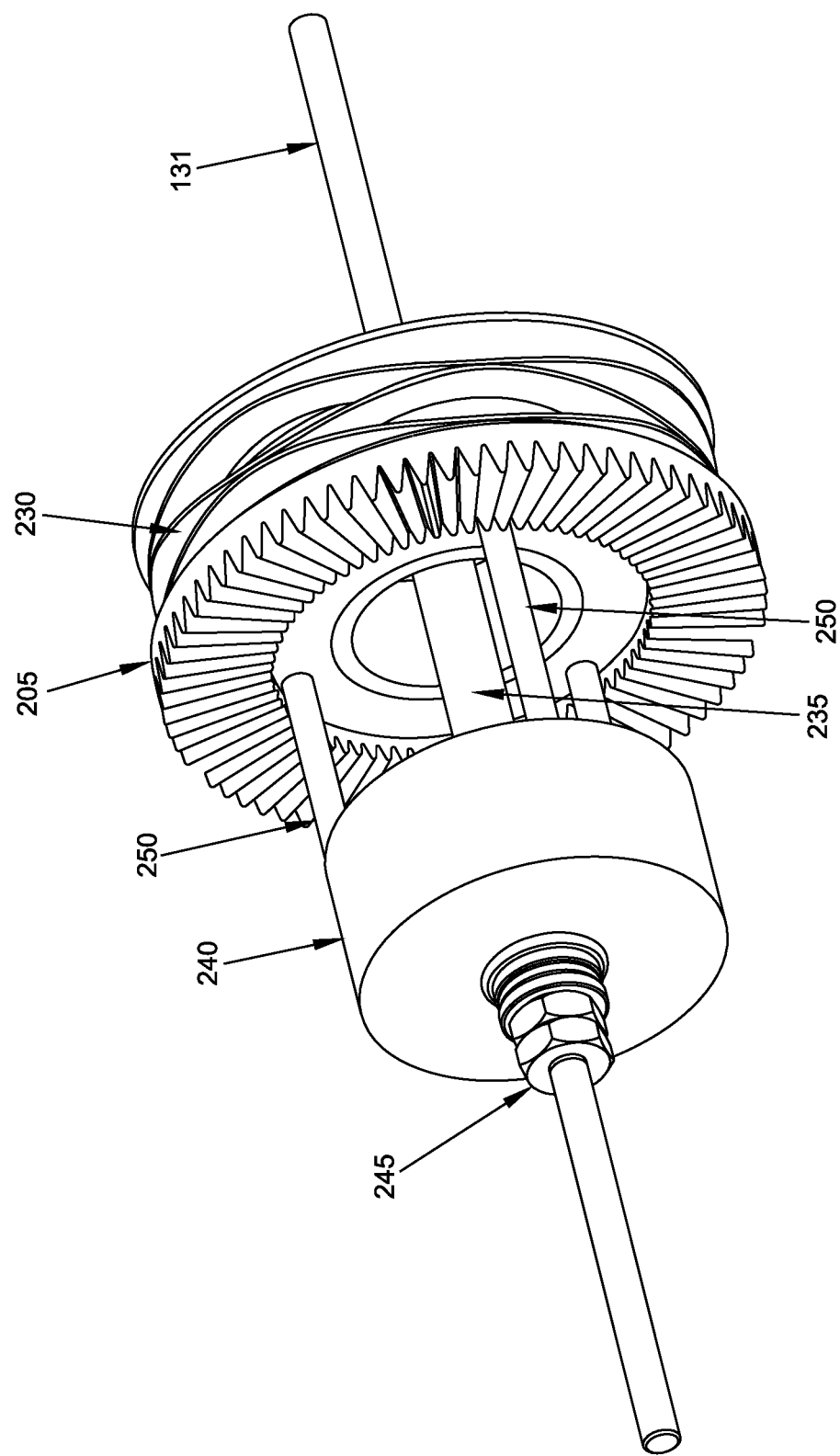

Looking next at FIGS. 21-31, locking mechanism 125 generally comprises a first locking gear 205 and a second locking gear 210. A housing 215 receives first locking gear 205 and second locking gear 210. First locking gear 205 and housing 215 are fixed against rotation relative to one another by tongues 220 on housing 215 (FIG. 27) which are received in corresponding recesses 225 in first locking gear 205 (FIG. 28). A spring 230 is captured between first locking gear 205 and housing 215. Spring 230 biases first locking gear 205 into locking engagement with second locking gear 210.

Locking mechanism 125 also comprises means for overcoming the bias of spring 230 so as to allow first locking gear 205 and second locking gear 210 to rotate relative to one another. More particularly, locking mechanism 125 comprises a sleeve 235 (FIG. 31) which is disposed coaxially over the rod 131 (of the rod linkage of actuator 130) which is associated with (i.e., extends through) that locking mechanism. A node 240 is mounted on sleeve 235, adjacent to mounts 245 which are secured to the associated rod 131 of the rod linkage of actuator 130, such that when the associated rod 131 of the rod linkage is moved (i.e., by pulling on lever 135) so that mounts 245 move toward second locking gear 210, node 240 is also moved toward second locking gear 210. A plurality of pins 250 extend through second locking gear 210 (FIG. 29), and between node 240 and first locking gear 205 (FIG. 31), so that when node 240 is moved toward second locking gear 210 (e.g., by the associated rod 131 of the rod linkage), first locking gear 205 is forced away from second locking gear 210 by pins 250, whereby to disengage first locking gear 205 from second locking gear 210 (and thereby allow first locking gear 205 and second locking gear 210 to rotate relative to one another).

Thus it will be seen that with locking mechanism 125, spring 230 normally biases first locking gear 205 into locking engagement with second locking gear 210, but the associated rod 131 of the rod linkage of actuator 130 may be used to move node 240 toward second locking gear 210, whereby to cause pins 250 to move first locking gear 205 out of engagement with second locking gear 210 and thereby allow first locking gear 205 and second locking gear 210 to rotate relative to one another.

Figure 32:
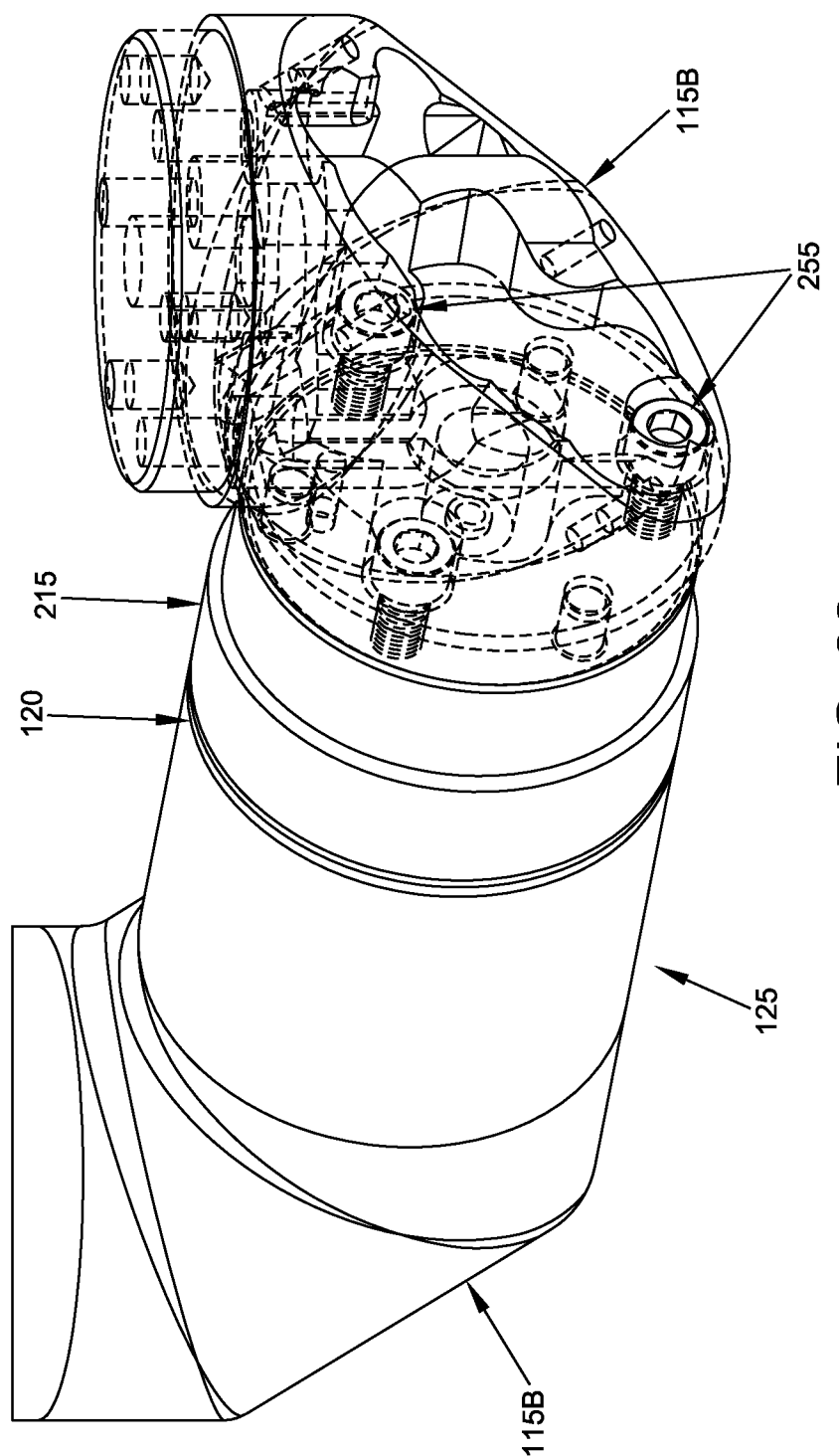
Figure 33:
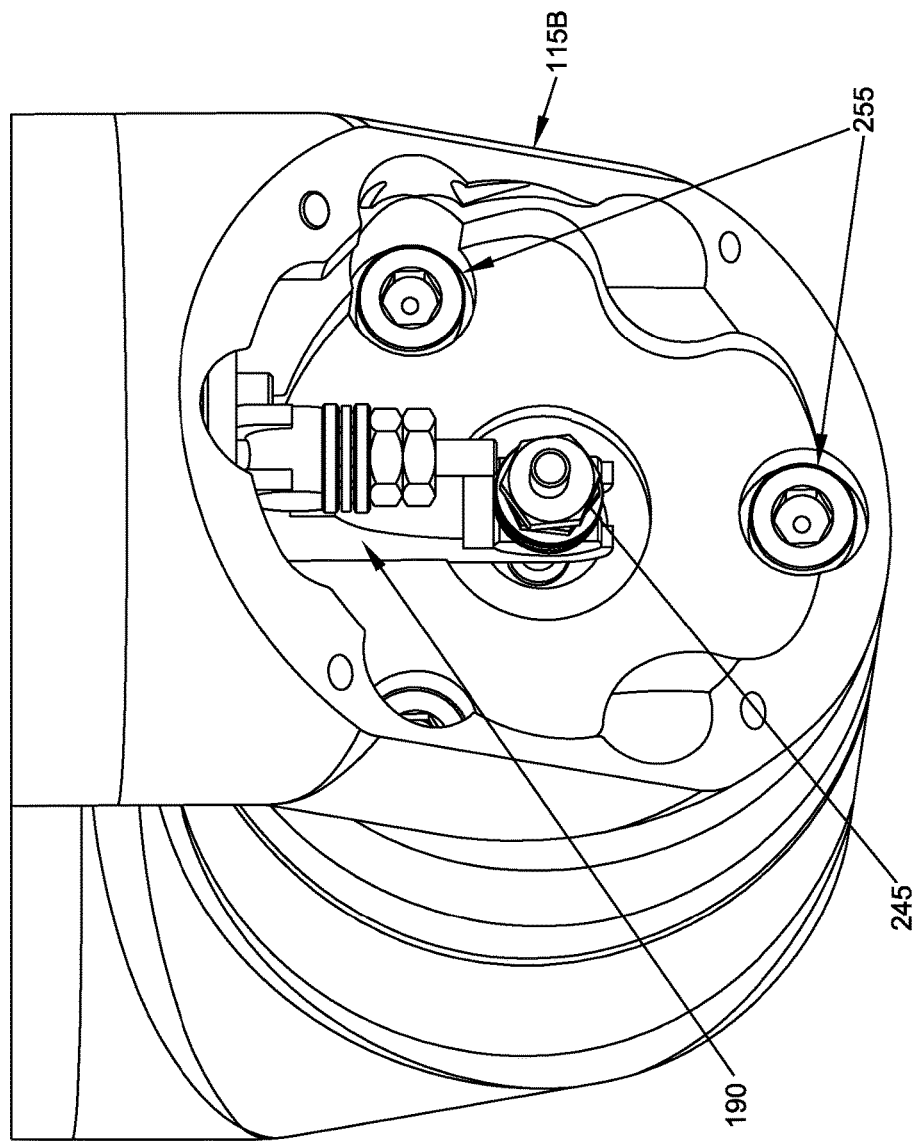

In accordance with the present invention, housing 215 of locking mechanism 125 is secured to an adjacent tubular element 115, e.g., by bolts 255 (FIGS. 32 and 33). Inasmuch as housing 215 is rotationally fixed to first locking gear 205, that adjacent tubular element 115 is itself rotationally fixed to first locking gear 205.

Figure 34:
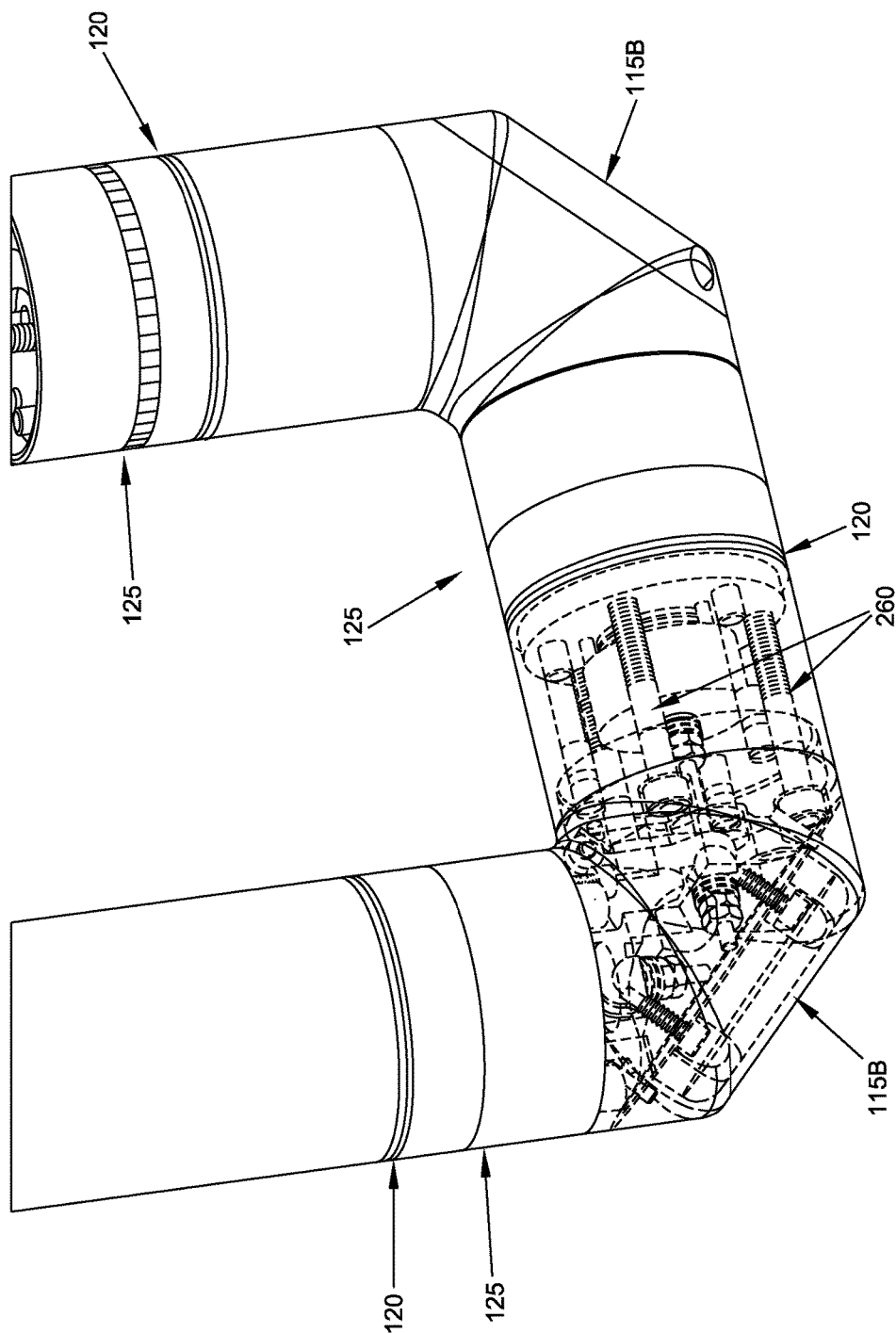
Figure 35:
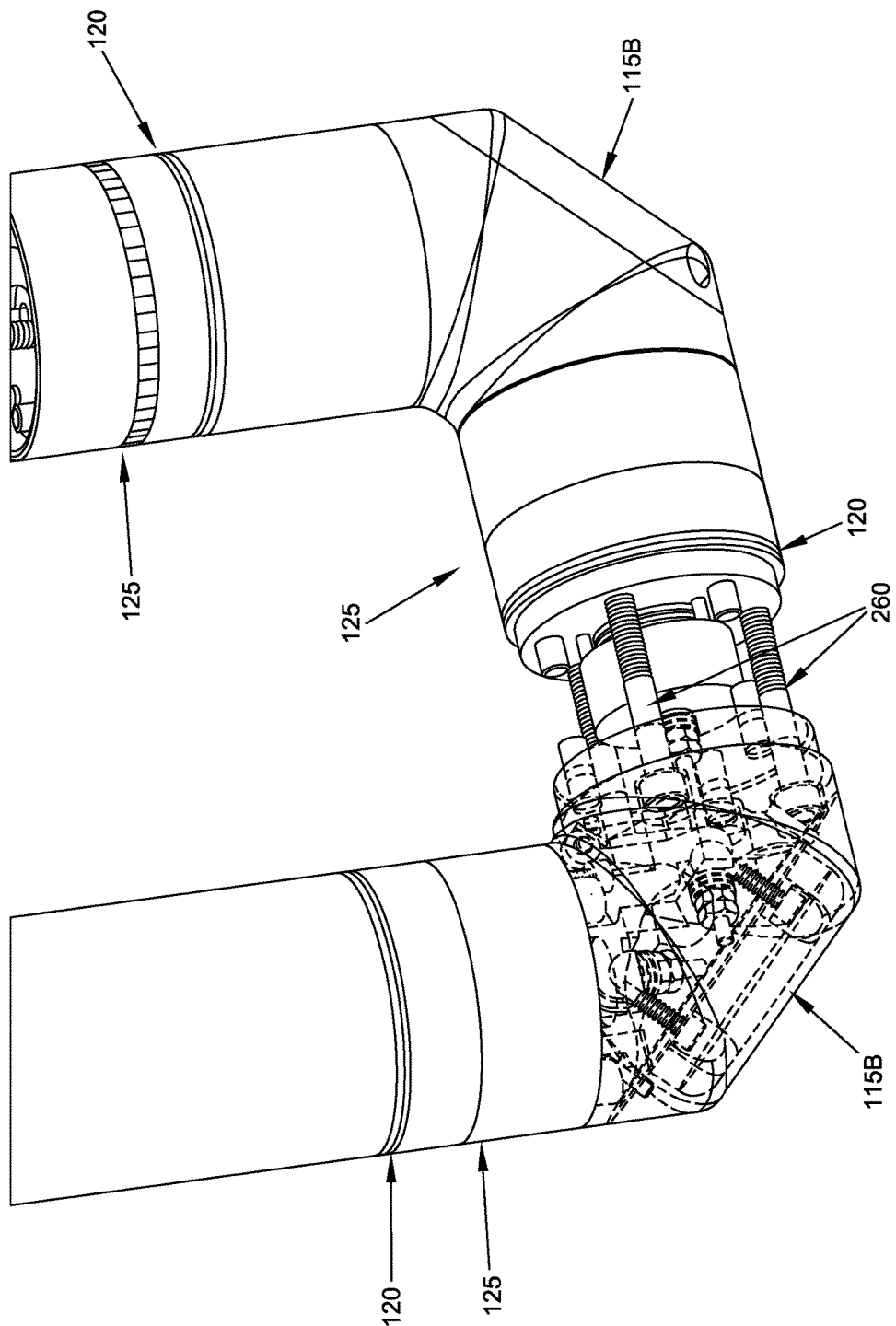
Figure 36:
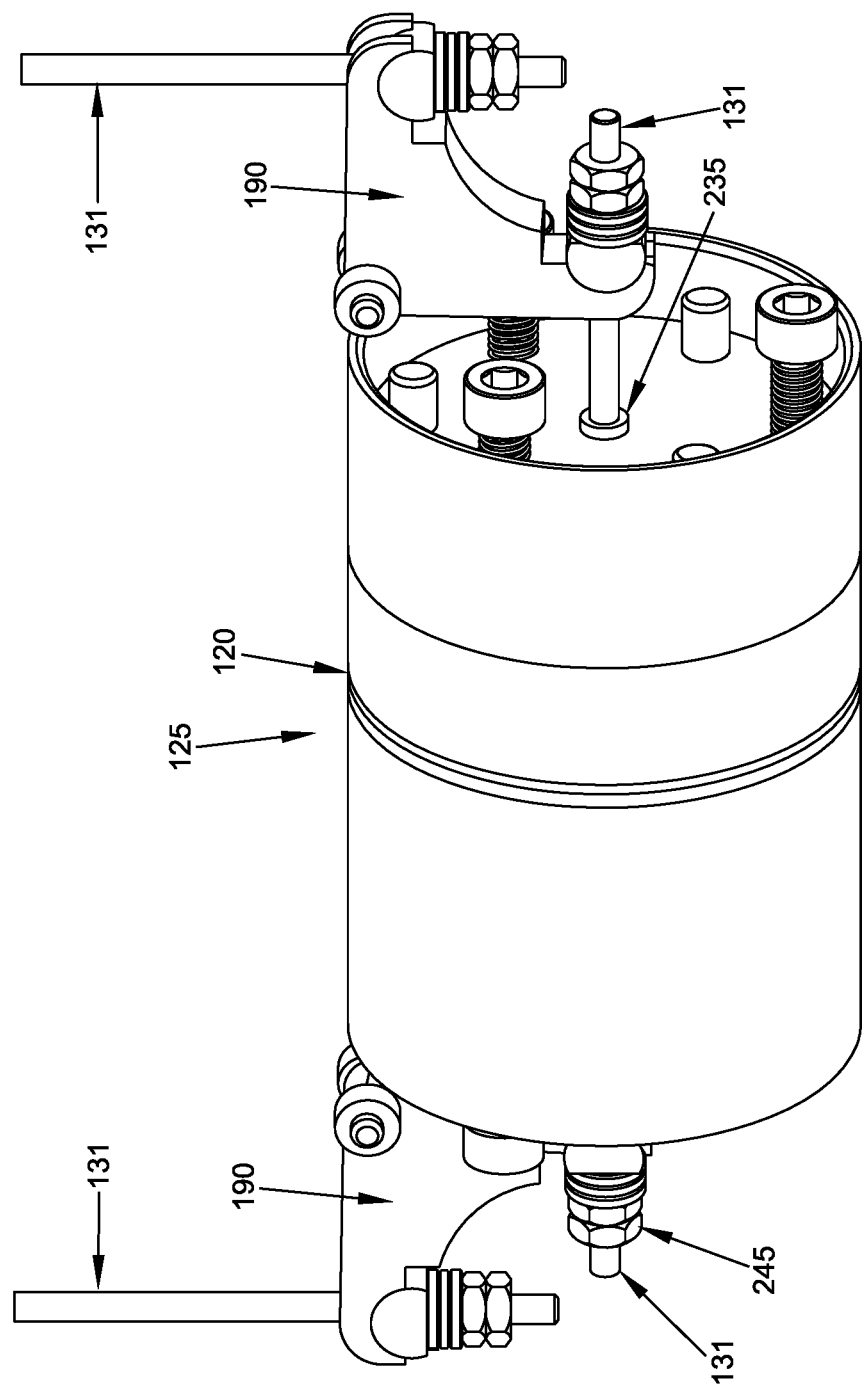

Also in accordance with the present invention, second locking gear 210 is secured to another adjacent tubular element 115, e.g., by bolts 260 (FIGS. 34 and 35).

On account of the foregoing construction, where a locking mechanism 125 is disposed at a joint 120 between a first tubular element 115 and a second tubular element 115, and where that first tubular element 115 is secured to the housing 215 of that locking mechanism 125 and the second tubular element 115 is secured to the second locking gear 210 of that locking mechanism 125, the first tubular element 115 and the second tubular element 115 are rotationally fixed relative to one another when no force is applied to the associated rod 131 of the rod linkage of actuator 130 (due to the bias imposed on first locking gear 205 by spring 230). However, when an appropriate force is applied to the associated rod 131 of the rod linkage of actuator 130 so as to overcome the force of spring 230 (i.e., so as to move first locking gear 205 out of engagement with second locking gear 210), the first tubular element 115 and the second tubular element 115 will be free to rotate relative to one another.

Thus it will be seen that with adjustable-position support arm 105 of the present invention, when no force is applied to lever 135, locking mechanisms 125 will hold tubular elements 115 locked about the joints 120 in a particular configuration. However, when force is applied to lever 135, the various rods 131 of the rod linkage of actuator 130 will simultaneously move within each locking mechanism 125, whereby to actuate (i.e., unlock) the locking mechanisms and thereby allow tubular elements 115 to be re-configured into another configuration. Thereafter releasing lever 135 will cause the locking mechanisms 125 to simultaneously return to their locked states, whereby to hold the tubular elements in their new configuration.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An adjustable-position support arm for a medical table, the adjustable-position support arm comprising:
   a plurality of tubular elements connected to one another in series at a plurality of joints;
   a locking mechanism disposed at each joint so that a first portion of the locking mechanism is secured to a first tubular element of that joint and a second portion of the locking mechanism is secured to the second tubular element of that same joint, wherein the locking mechanism is normally configured in a locked condition so as to prevent rotation of the first tubular element relative to the second tubular element, and further wherein the locking mechanism may be selectively reconfigured in an unlocked condition so that the first tubular element is rotatable relative to the second tubular element; and
   an actuator for simultaneously reconfiguring all of the locking mechanisms from their locked condition to their unlocked condition, whereby to permit the plurality of tubular elements to be rotated about the plurality of joints;
   wherein the locking mechanism comprises a male locking gear, a locking guide spindle, a female locking gear, and a spring;
   wherein the male locking gear and the locking guide spindle are arranged so as to allow longitudinal movement between the male locking gear and the locking guide spindle but to prevent rotational movement between the male locking gear and the locking guide spindle;
   wherein the spring is arranged to bias the male locking gear into locking engagement with the female locking gear;
   wherein the actuator is arranged to selectively move the male locking gear out of locking engagement with the female locking gear; and
   wherein the locking guide spindle is secured to the first tubular element of a joint and the female locking gear is secured to the second tubular element of that same joint.

2. An adjustable-position support arm according to claim 1 wherein at least one tubular element is straight.

3. An adjustable-position support arm according to claim 1 wherein at least one tubular element is angled.

4. An adjustable-position support arm according to claim 3 wherein at least one tubular element is angled at a right angle.

5. An adjustable-position support arm according to claim 1 wherein a plurality of the tubular elements are straight and a plurality of the tubular elements are angled.

6. An adjustable-position support arm according to claim 5 wherein each straight tubular element is separated from another straight tubular element by an angled tubular element.

7. An adjustable-position support arm according to claim 1 further comprising a mount secured to one of the tubular elements for securing that tubular element to a medical table.

8. An adjustable-position support arm according to claim 1 further comprising a mount secured to one of the tubular elements for securing a patient support to that tubular element.

9. An adjustable-position support arm according to claim 1 wherein the actuator comprises an elongated component extending through the plurality of tubular elements and through each locking mechanism.

10. An adjustable-position support arm according to claim 9 wherein one end of the elongated component is secured to a lever.

11. An adjustable-position support arm according to claim 9 wherein the elongated component comprises a cable.

12. An adjustable-position support arm according to claim 11 further comprising a plurality of nodes secured to the cable, and further wherein the nodes are arranged to apply a force to the locking mechanisms when the cable is moved, whereby to reconfigure the locking mechanisms from their locked condition to their unlocked condition.

13. An adjustable-position support arm for a medical table, the adjustable-position support arm comprising:
    a plurality of tubular elements connected to one another in series at a plurality of joints;
    a locking mechanism disposed at each joint so that a first portion of the locking mechanism is secured to a first tubular element of that joint and a second portion of the locking mechanism is secured to the second tubular element of that same joint, wherein the locking mechanism is normally configured in a locked condition so as to prevent rotation of the first tubular element relative to the second tubular element, and further wherein the locking mechanism may be selectively reconfigured in an unlocked condition so that the first tubular element is rotatable relative to the second tubular element; and
    an actuator for simultaneously reconfiguring all of the locking mechanisms from their locked condition to their unlocked condition, whereby to permit the plurality of tubular elements to be rotated about the plurality of joints;

wherein the locking mechanism comprises a first locking gear, a second locking gear, a housing receiving the first locking gear and the second locking gear, and a spring;

wherein the first locking gear and the housing are arranged so as to allow longitudinal movement between the first locking gear and the housing but to prevent rotational movement between the first locking gear and the housing;

wherein the spring is arranged to bias the first locking gear into locking engagement with the second locking gear;

wherein the actuator is arranged to selectively move the first locking gear out of locking engagement with the second locking gear; and wherein the housing is secured to the first tubular element of a joint and the second locking gear is secured to the second tubular element of that same joint.

14. An adjustable-position support arm according to claim 13 wherein at least one tubular element is straight.

15. An adjustable-position support arm according to claim 13 wherein at least one tubular element is angled.

16. An adjustable-position support arm according to claim 15 wherein at least one tubular element is angled at a right angle.

17. An adjustable-position support arm according to claim 13 wherein a plurality of the tubular elements are straight and a plurality of the tubular elements are angled.

18. An adjustable-position support arm according to claim 17 wherein each straight tubular element is separated from another straight tubular element by an angled tubular element.

19. An adjustable-position support arm according to claim 13 further comprising a mount secured to one of the tubular elements for securing that tubular element to a medical table.

20. An adjustable-position support arm according to claim 13 further comprising a mount secured to one of the tubular elements for securing a patient support to that tubular element.

21. An adjustable-position support arm according to claim 13 wherein the actuator comprises an elongated component extending through the plurality of tubular elements and through each locking mechanism.

22. An adjustable-position support arm according to claim 21 wherein one end of the elongated component is secured to a lever.

23. An adjustable-position support arm according to claim 21 wherein the elongated component comprises a cable.

24. An adjustable-position support arm according to claim 23 further comprising a plurality of nodes secured to the cable, and further wherein the nodes are arranged to apply a force to the locking mechanisms when the cable is moved, whereby to reconfigure the locking mechanisms from their locked condition to their unlocked condition.

* * * * *